(12) United States Patent
Lin et al.

(10) Patent No.: US 10,596,171 B2
(45) Date of Patent: Mar. 24, 2020

(54) CAP-DEPENDENT ENDONUCLEASE INHIBITORS

(71) Applicants: TaiGen Biotechnology Co., Ltd., Taipei (TW); Ming-Chu Hsu, Santa Clara, CA (US)

(72) Inventors: Chu-Chung Lin, Taipei (TW); Hung-Chuan Chen, Taipei (TW); Chiayn Chiang, Taipei (TW); Chi-Feng Yen, Taipei (TW); Ming-Chu Hsu, Santa Clara, CA (US)

(73) Assignee: TaiGen Biotechnology Co., Ltd., Taipei (TW)

( * ) Notice: Subject to any disclaimer, the term of this patent is extended or adjusted under 35 U.S.C. 154(b) by 0 days.

(21) Appl. No.: 16/251,652

(22) Filed: Jan. 18, 2019

(65) Prior Publication Data

US 2019/0224198 A1   Jul. 25, 2019

Related U.S. Application Data

(60) Provisional application No. 62/620,065, filed on Jan. 22, 2018.

(51) Int. Cl.
*A61K 31/5025* (2006.01)
*A61P 31/16* (2006.01)

(52) U.S. Cl.
CPC .......... *A61K 31/5025* (2013.01); *A61P 31/16* (2018.01)

(58) Field of Classification Search
CPC .............................. A61K 31/5025; A61P 31/16
See application file for complete search history.

(56) References Cited

U.S. PATENT DOCUMENTS 9,815,835 B2   11/2017   Akiyama et al.

FOREIGN PATENT DOCUMENTS

| JP | 2017137291 | * | 8/2017 |
| JP | 2017137291 | A | 8/2017 |
| WO | WO-2012/039414 | A1 | 3/2012 |
| WO | WO-2017/072341 | A1 | 5/2017 |
| WO | WO-2017/109088 | A1 | 6/2017 |

OTHER PUBLICATIONS

Jones et al "A Novel Endonuclease Inhibitor Exhibits Broad-Spectrum Anti-Influenza Virus Activity In Vitro" Antimicrobial Agents and Chemotherapy vol. 60, pp. 5504-5514, 2016.

* cited by examiner

*Primary Examiner* — Alexander R Pagano
*Assistant Examiner* — Ebenezer O Sackey
(74) *Attorney, Agent, or Firm* — Cesari and McKenna, LLP

(57) ABSTRACT

Provided is a compound of Formula (I) below, or a pharmaceutically acceptable salt, metabolite, or prodrug thereof:

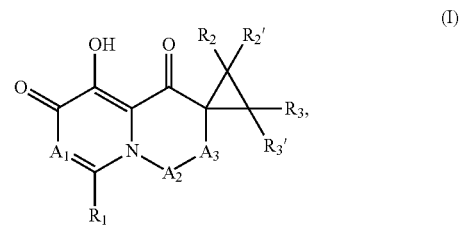

(I)

wherein: $A_1$ is $CR_4$ or N; $A_2$ is $CR_5R_6$ or $NR_7$; $A_3$ is $CR_5'R_6'$ or $NR_7'$; each of $R_1$, $R_2$, $R_2'$, $R_3$, $R_3'$, $R_4$, $R_5$, $R_5'$, $R_6$, $R_6'$, $R_7$, and $R_7'$, independently, is hydrogen, deuterium, halogen, cyano, hydroxyl, carboxyl, amino, formyl, nitro, $C_{1-6}$ alkyl, $C_{2-6}$ alkenyl, $C_{2-6}$ alkynyl, $C_{1-6}$ alkoxy, $C_{2-6}$ alkenyloxy, $C_{1-6}$ alkylcarbonyl, $C_{1-6}$ alkyloxycarbonyl, $C_{1-6}$ alkylamine, $C_{3-20}$ carbocyclyl, or $C_{3-20}$ heterocyclyl; or $R_5$ and $R_6$, $R_5'$ and $R_6'$, or $R_5$ and $R_5'$, together with the adjacent atom to which they are each attached, form $C_{3-10}$ carbocyclyl or $C_{3-10}$ heterocyclyl. Further provided are a method of using the above-described compound, or the pharmaceutically acceptable salt, metabolite, or prodrug thereof for treating influenza and a pharmaceutical composition containing same.

18 Claims, No Drawings

CAP-DEPENDENT ENDONUCLEASE INHIBITORS

CROSS-REFERENCE TO RELATED APPLICATIONS

This application claims priority of U.S. Provisional Patent Application No. 62/620,065, filed on Jan. 22, 2018.

TECHNICAL FIELD

The present disclosure is related to heterocyclic compounds that have cap-dependent endonuclease inhibitory activity, prodrugs thereof, and the use thereof for treating influenza.

BACKGROUND

The RNA polymerase of influenza viruses contains a cap-dependent endonuclease domain that cleaves host mRNAs to produce capped RNA fragments to serve as primers for initiating viral mRNA synthesis.

Translation of viral mRNAs by host ribosomes requires that the viral mRNAs be 5'-capped. This is achieved in cells infected with influenza viruses by a "cap-snatching" mechanism in which the cap-dependent endonuclease cleaves 5'-caps from host mRNAs, which are then utilized as transcription primers (10-13 nucleotides). These capped RNA primers are used for synthesizing mRNAs encoding viral proteins.

Inhibiting the activity of cap-dependent endonuclease results in suppression of virus proliferation. As such, the cap-dependent endonuclease is a potential biological target for identifying effective anti-influenza agents.

Various heterocyclic compounds have been used as cap-dependent endonuclease inhibitors. Yet, conventional heterocyclic compounds exhibit poor pharmacological properties, e.g., poor efficacy, low solubility, and poor bioavailability, thereby rendering them impractical for use as therapeutics for treating influenza.

There is a need to develop new cap-dependent endonuclease inhibitors for treating influenza that do not suffer from the above-described drawbacks.

SUMMARY

The present disclosure relates to heterocyclic compounds as cap-dependent endonuclease inhibitors for treating influenza. Unexpectedly, these compounds demonstrate high potency in inhibiting the activity of cap-dependent endonuclease.

An aspect of this disclosure is drawn to the compounds of Formula (I) below, or pharmaceutically acceptable salts, metabolites, or prodrugs thereof:

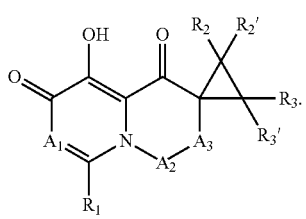

(I)

In this formula, $R_1$ is hydrogen, deuterium, halogen, cyano, hydroxyl, carboxyl, amino, $C_{1-6}$ alkyl, $C_{2-6}$ alkenyl, $C_{2-6}$ alkynyl, $C_{1-6}$ alkoxy, $C_{1-6}$ alkylamine, $C_{3-20}$ carbocyclyl or $C_{3-20}$ heterocyclyl; each of $R_2$, $R_2'$, $R_3$, and $R_3'$, independently, is hydrogen, deuterium, halogen, cyano, hydroxyl, carboxyl, amino, formyl, nitro, $C_{1-6}$ alkyl, $C_{2-6}$ alkenyl, $C_{2-6}$ alkynyl, $C_{1-6}$ alkoxy, $C_{2-6}$ alkenyloxy, $C_{1-6}$ alkylcarbonyl, $C_{1-6}$ alkyloxycarbonyl, $C_{1-6}$ alkylamine, $C_{3-20}$ carbocyclyl, or $C_{3-20}$ heterocyclyl; $A_1$ is $CR_4$ or N; $A_2$ is $CR_5R_6$ or $NR_7$; $A_3$ is $CR_5'R_6'$ or $NR_7'$; $R_4$ is hydrogen, deuterium, halogen, cyano, hydroxyl, carboxyl, amino, $C_{1-6}$ alkyl, $C_{2-6}$ alkenyl, $C_{2-6}$ alkynyl, $C_{1-6}$ alkoxy, $C_{3-20}$ carbocyclyl, or $C_{3-20}$ heterocyclyl; and each of $R_5$, $R_5'$, $R_6$, $R_6'$, $R_7$, and $R_7'$, independently, is hydrogen, deuterium, halogen, cyano, hydroxyl, carboxyl, $C_{1-6}$ alkyl, $C_{2-6}$ alkenyl, $C_{2-6}$ alkynyl, $C_{1-6}$ alkoxy, $C_{3-20}$ carbocyclyl, or $C_{3-20}$ heterocyclyl; or $R_5$ and $R_6$, $R_5'$ and $R_6'$, or $R_5$ and $R_5'$, together with the adjacent atom to which they are each attached, form $C_{3-10}$ carbocyclyl or $C_{3-10}$ heterocyclyl. Of note, each of $C_{1-6}$ alkyl, $C_{2-6}$ alkenyl, $C_{2-6}$ alkynyl, $C_{1-6}$ alkoxy, $C_{2-6}$ alkenyloxy, $C_{1-6}$ alkylcarbonyl, $C_{1-6}$ alkyloxycarbonyl, $C_{1-6}$ alkylamine, $C_{3-10}$ carbocyclyl, $C_{3-10}$ heterocyclyl, $C_{3-20}$ carbocyclyl, and $C_{3-20}$ heterocyclyl is optionally substituted with 1 to 5 moieties of deuterium, halogen, hydroxyl, cyano, amino, nitro, carboxyl, $C_{1-6}$ alkyl, $C_{1-6}$ alkoxy, $C_{1-6}$ alkylamino, $C_{1-6}$ alkyl($C_{3-10}$ carbocyclyl), $C_{1-6}$ alkyl($C_{3-10}$ heterocyclyl), $C_{1-6}$ alkoxy($C_{3-10}$ carbocyclyl), $C_{1-6}$ alkoxy($C_{3-10}$ heterocyclyl), $C_{3-10}$ carbocyclyl, or $C_{3-10}$ heterocyclyl.

The compounds, salts, metabolites, or prodrugs described above include the compounds themselves, as well as their polymorphs, stereoisomers and solvates, if applicable. A salt, for example, can be formed between an anion and a positively charged group (e.g., amino) on a compound having the above formula. Suitable anions include chloride, bromide, iodide, sulfate, nitrate, phosphate, citrate, methanesulfonate, trifluoroacetate, acetate, malate, tosylate, tartrate, fumarate, glutamate, glucuronate, lactate, glutarate, and maleate. Likewise, a salt can also be formed between a cation and a negatively charged group (e.g., carboxylate) on a compound also having the above formula. Suitable cations include sodium ions, potassium ions, magnesium ions, calcium ions, and an ammonium cation such as a tetramethylammonium ion. The compounds also include those salts containing quaternary nitrogen atoms. For calculation simplicity, unless otherwise stated, the weight of a compound mentioned herein refers to that of the free base form of that compound.

Examples of prodrugs include esters and other pharmaceutically acceptable derivatives, which, upon administration to a subject, are capable of providing active compounds. Typically, a prodrug of this disclosure has the following formula:

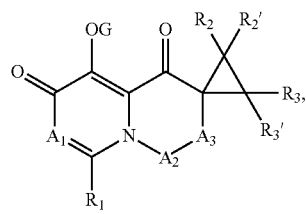

in which G is a group for forming a prodrug, which can be converted to a compound of Formula (I) in physiological conditions. Examples of G include, but are not limited to, —C(R$_9$R$_9$')—O—CO—R$_{10}$, —C(R$_9$R$_9$')—O—CO—O—R$_{10}$, —C(R$_9$R$_9$')—NR$_{11}$—C(=O)—CO—O—R$_{10}$, —C(R$_9$R$_9$')—O—CO—C(R$_9$R$_9$')—NR$_{11}$—CO—O—R$_{10}$, —C(R$_9$R$_9$')—C(R$_9$R$_9$')—O—CO—R$_{10}$, —C(R$_9$R$_9$')—R$_{10}$, —C(=O)—O—R$_{10}$, —C(=O)—R$_{10}$, —C(=O)—O-alkylene-O—R$_{10}$, —C(=O)—NR$_{10}$R$_{11}$, and —P(=O)(R$_{12}$R$_{13}$), in which each of R$_9$, R$_9$', and R$_{11}$, independently, is hydrogen or C$_{1-8}$ alkyl; R$_{10}$ is C$_{1-8}$ alkyl, C$_{3-10}$ carbocyclyl, or C$_{3-10}$ heterocyclyl; R$_{12}$ is C$_{1-8}$ alkoxy; and R$_{13}$ is C$_{1-8}$ alkoxy or C$_{1-8}$ alkylamine. A$_1$, A$_2$, A$_3$, R$_1$, R$_2$, R$_2$', R$_3$, and R$_3$' have the same definition as in Formula (I).

A solvate refers to a complex formed between an active compound and a pharmaceutically acceptable solvent. Examples of pharmaceutically acceptable solvents include water, ethanol, isopropanol, ethyl acetate, acetic acid, and ethanolamine.

Another aspect of this disclosure is a pharmaceutical composition containing a compound, salt, metabolite, or prodrug described above and one or more pharmaceutically acceptable ingredients. The pharmaceutical acceptable ingredients are diluents, disintegrants, binders, lubricants, glidants, surfactants, or a combination thereof. The pharmaceutical composition can be used for treating influenza.

This disclosure also encompasses use of one or more of the above-described compounds of Formula (I), as well as their salts, metabolites or prodrugs, for the manufacture of a medicament for treating influenza.

Still another aspect of this disclosure is a method of preparing a compound of Formula (I), or a pharmaceutically acceptable salt, metabolite, or prodrug thereof.

A further aspect of this disclosure is a method for treating influenza associated with cap-dependent endonuclease. The method includes administering to a subject in need thereof an effective amount of one or more of the compounds, salts, metabolites or prodrugs described above.

The term "treating" or "treatment" refers to administering one or more of the compounds, salts, metabolites or prodrugs to a subject, who has an above-described disease, i.e., influenza, a symptom of such a disease, or a predisposition toward such a disease, with the purpose to confer a therapeutic effect, e.g., to cure, relieve, alter, affect, ameliorate, or prevent the above-described disease, the symptom thereof, or the predisposition toward it. "An effective amount" refers to the amount of an active compound, salt, metabolite, or prodrug that is required to confer the therapeutic effect. Effective doses will vary, as recognized by those skilled in the art, depending on the types of disease treated, route of administration, excipient usage, and the possibility of co-usage with other therapeutic treatment.

To practice the method of the present disclosure, a composition having one or more of the above-described compounds, salts, metabolites or prodrugs can be administered parenterally, orally, nasally, rectally, topically, or buccally. The term "parenteral" as used herein refers to subcutaneous, intracutaneous, intravenous, intraperitoneal, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or di-glycerides). Fatty acids, such as oleic acid and its glyceride derivatives, are useful in the preparation of injectables, as naturally pharmaceutically acceptable oils, such as olive oil and castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens and Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include, among others, lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

Of note, a composition having one or more of the above-described compounds, salts, metabolites and prodrugs can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active 1,5-diphenyl-penta-1,4-dien-3-one compound. Examples of other carriers include colloidal silicon oxide, magnesium stearate, cellulose, sodium lauryl sulfate, and D&C Yellow #10.

Details of the present disclosure and practice thereof are set forth in the description below. Note that other features, objects, and advantages of the disclosure will be apparent from the following detailed description of several embodiments, as well as from the appending claims.

DETAILED DESCRIPTION

Disclosed in detail are compounds of Formula (I) below or pharmaceutically acceptable salts, metabolites, or prodrugs thereof:

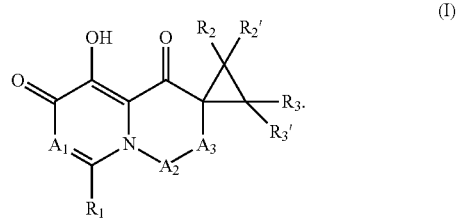

To reiterate, $R_1$ is hydrogen, deuterium, halogen, cyano, hydroxyl, carboxyl, amino, $C_{1-6}$ alkyl, $C_{2-6}$ alkenyl, $C_{2-6}$ alkynyl, $C_{1-6}$ alkoxy, $C_{1-6}$ alkylamine, $C_{3-20}$ carbocyclyl or $C_{3-20}$ heterocyclyl; each of $R_2$, $R_2'$, $R_3$, and $R_3'$, independently, is hydrogen, deuterium, halogen, cyano, hydroxyl, carboxyl, amino, formyl, nitro, $C_{1-6}$ alkyl, $C_{2-6}$ alkenyl, $C_{2-6}$ alkynyl, $C_{1-6}$ alkoxy, $C_{2-6}$ alkenyloxy, $C_{1-6}$ alkylcarbonyl, $C_{1-6}$ alkyloxycarbonyl, $C_{1-6}$ alkylamine, $C_{3-20}$ carbocyclyl or $C_{3-20}$ heterocyclyl; $A_1$ is $CR_4$ or N; $A_2$ is $CR_5R_6$ or $NR_7$; $A_3$ is $CR_5'R_6'$ or $NR_7'$; $R_4$ is hydrogen, deuterium, halogen, cyano, hydroxyl, carboxyl, amino, $C_{1-6}$ alkyl, $C_{2-6}$ alkenyl, $C_{2-6}$ alkynyl, $C_{1-6}$ alkoxy, $C_{3-20}$ carbocyclyl, or $C_{3-20}$ heterocyclyl; and each of $R_5$, $R_5'$, $R_6$, $R_6'$, $R_7$, and $R_7'$, independently, is hydrogen, deuterium, halogen, cyano, hydroxyl, carboxyl, $C_{1-6}$ alkyl, $C_{2-6}$ alkenyl, $C_{2-6}$ alkynyl, $C_{1-6}$ alkoxy, $C_{3-20}$ carbocyclyl, or $C_{3-20}$ heterocyclyl; or $R_5$ and $R_6$, $R_5'$ and $R_6'$, or $R_5$ and $R_5'$, together with the adjacent atom to which they are each attached, form $C_{3-10}$ carbocyclyl or $C_{3-10}$ heterocyclyl. Note that each of $C_{1-6}$ alkyl, $C_{2-6}$ alkenyl, $C_{2-6}$ alkynyl, $C_{1-6}$ alkoxy, $C_{2-6}$ alkenyloxy, $C_{1-6}$ alkylcarbonyl, $C_{1-6}$ alkyloxycarbonyl, $C_{1-6}$ alkylamine, $C_{3-10}$ carbocyclyl, $C_{3-10}$ heterocyclyl, $C_{3-20}$ carbocyclyl, and $C_{3-20}$ heterocyclyl is optionally substituted with 1 to 5 moieties of deuterium, hydroxyl, cyano, amino, nitro, carboxyl, $C_{1-6}$ alkyl, $C_{1-6}$ alkoxy, $C_{1-6}$ alkylamino, $C_{1-6}$ alkyl($C_{3-10}$ carbocyclyl), $C_{1-6}$ alkyl($C_{3-10}$ heterocyclyl), $C_{1-6}$ alkoxy($C_{3-10}$ carbocyclyl), $C_{1-6}$ alkoxy($C_{3-10}$ heterocyclyl), $C_{3-10}$ carbocyclyl, or $C_{3-10}$ heterocyclyl.

The term "halogen" herein refers to a fluoro, chloro, bromo, or iodo group. The term "hydroxyl" refers to an —OH group. The term "cyano" refers to a —CN group. The term "amino" refers to an —NH$_2$ group. The term "nitro" refers to an —NO$_2$ group. The term "carboxyl" refers to a —COOH group.

The term "$C_{1-6}$ alkyl" (alone or in combination with another term) refers to a straight- or branched-chain saturated hydrocarbyl substituent containing 1 to 6 (e.g., 1 to 4) carbon atoms. Examples of $C_{1-6}$ alkyl include methyl, ethyl, n-propyl, isopropyl, n-butyl, isobutyl, sec-butyl, tert-butyl, n-pentyl, and the like. The term "$C_{2-6}$ alkenyl" (alone or in combination with another term) refers to a straight- or branched-chain hydrocarbyl substituent containing 2 to 6 (e.g., 2 to 4) carbon atoms and one or more double bonds. Examples of $C_{2-6}$ alkenyl include vinyl, allyl, propenyl, isopropenyl, butenyl, isobutenyl, prenyl, butadienyl, pentenyl, isopentenyl, pentadienyl, and the like. The term "$C_{2-6}$ alkynyl" (alone or in combination with another term) refers to a straight- or branched-chain hydrocarbyl substituent containing 2 to 6 (e.g., 2 to 4) carbon atoms and one or more triple bonds. Examples of $C_{2-6}$ alkynyl include ethynyl, propynyl, butynyl, pentynyl, and the like.

The term "$C_{1-6}$ alkoxy" (alone or in combination with another term) refers to the group —OR wherein R is $C_{1-6}$ alkyl. Examples of $C_{1-6}$ alkoxy include methoxy, ethoxy, n-propoxy, isopropoxy, n-butoxy, iso-butoxy, sec-butoxy, and tert-butoxy.

The term "$C_{1-6}$ alkylamine" (alone or in combination with another term) refers to the group —NHR wherein R is $C_{1-6}$ alkyl. Examples of $C_{1-6}$ alkylamine include methylamino, ethylamino, and isopropylamino.

The term "$C_{3-20}$ carbocyclyl" (alone or in combination with another term) refers to a saturated cyclic (i.e., "cycloalkyl"), partially saturated cyclic (i.e., "cycloalkenyl"), or completely unsaturated (i.e., "aryl") hydrocarbyl substituent containing from 3 to 20 carbon ring atoms (e.g., 3 to 10, $C_{3-10}$ carbocyclyl; 3 to 8, $C_{3-8}$ carbocyclyl; and 5 to 6, $C_{5-6}$ carbocyclyl).

The term "cycloalkyl" (alone or in combination with another term) herein refers to a saturated cyclic hydrocarbyl substituent containing from 3 to 20 carbon ring atoms. A cycloalkyl can be a single carbon ring, which typically contains from 3 to 10 carbon ring atoms, more typically from 3 to 8 ring atoms, and even more typically 5 to 6 ring atoms. Examples of single-ring cycloalkyl include cyclopropyl, cyclobutyl, cyclopentyl, cyclohexyl, cycloheptyl, cyclooctyl, cyclononyl and cyclodecyl. A cycloalkyl can alternatively be a polycyclic ring. The term "cycloalkenyl" (alone or in combination with another term) refers to a partially saturated cyclic hydrocarbyl substituent containing from 3 to 20 carbon ring atoms. A cycloalkenyl may be a single carbon ring, which typically contains from 3 to 10 carbon ring atoms, more typically from 3 to 6 ring atoms, and even more typically 5 to 6 ring atoms. Examples of single-ring cycloalkenyl include cyclopropenyl, cyclobutenyl, cyclopentenyl, cyclohexenyl, cycloheptynyl, cyclooctynyl and cyclohexadienyl. A cycloalkenyl may alternatively be a polycyclic ring. The term "aryl" (alone or in combination with another term) refers to an aromatic carbocyclyl containing from 6 to 20 carbon ring atoms. An aryl may be monocyclic or polycyclic. In the case of a polycyclic aromatic ring, only one ring of the polycyclic system is required to be unsaturated while the remaining ring(s) may be saturated, partially saturated or unsaturated. Examples of aryl include phenyl, naphthalenyl, indenyl, indanyl, and tetrahydronapthyl, fluorenyl, adamantyl.

A carbocyclyl can also be a polycyclic ring structure (i.e., containing two or more rings selected from "cycloalkyl", "cycloalkenyl", and "aryl"). Examples of a polycyclic carbocyclyl include bridged, fused, and spirocyclic carbocyclyls. In a bridged carbocyclyl, the rings share at least two common non-adjacent atoms. In a fused-ring carbocyclyl system, two or more rings may be fused together, such that the two rings share one common bond. Examples of fused-ring carbocyclyls include indanyl, indenyl, tetrahydronaphthyl, and fluorenyl. A typical fused-ring carbocyclyl is

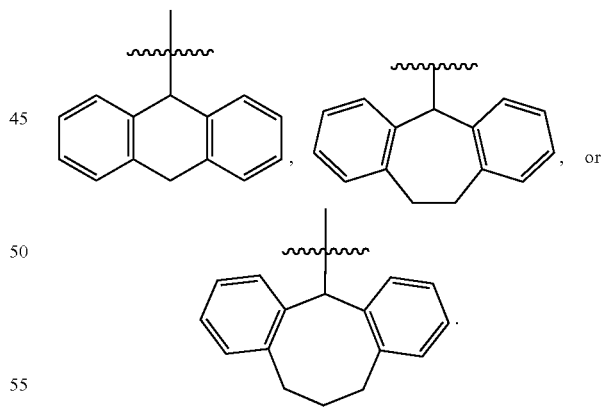

The term "$C_{3-20}$ heterocyclyl" (alone or in combination with another term) refers to a saturated (i.e., "heterocycloalkyl"), partially saturated (i.e., "heterocycloalkenyl"), or completely unsaturated (i.e., "heteroaryl") ring structure containing a total of 3 to 20 ring atoms, wherein at least one of the ring atoms is a heteroatom selected from the group consisting of O, N, and S. In one embodiment, heterocyclyl contains 1 to 4 (e.g., 1 to 2) heteroatoms of O, N, and S. The term "heterocycloalkyl" (alone or in combination with another term) refers to a saturated heterocyclyl. The term "heterocycloalkenyl" (alone or in combination with another term) refers to a partially saturated heterocyclyl. The term "heteroaryl" (alone or in combination with another term) refers to an aromatic heterocyclyl.

A heterocyclyl moiety may be a monocyclic structure, which typically contains from 3 to 10 ring atoms (i.e., $C_{3-10}$ heterocyclyl), more typically from 3 to 8 ring atoms (i.e., $C_{3-8}$ heterocyclyl), and even more typically 5 to 6 ring atoms (i.e., $C_{5-6}$ heterocyclyl). Examples of monocyclic heterocyclyl include furanyl, tetrafuranyl, thiophenyl, pyrrolyl, imidazolyl, pyrrolinyl, pyrrolidinyl, imidazolyl, imidazolinyl, imidazolidinyl, pyridyl, dihydropyridyl, tetrahydropyridyl, pyrazinyl, pyrazolyl, pyrazolinyl, pyridazinyl, tetrahydropyridazinyl, pyrazolidinyl, triazolyl, tetrazolyl, oxazolyl, oxazolidinyl, isoxazolidinyl, isoxazolyl, thiazolyl, isothiazolyl, dihydrothiazolyl, tetrahydrothiazolyl, tetrahydroisothiazolyl, thiazolinyl, isothiazolinyl, thiazolidinyl, thianyl, thiazolidinyl, isothiazolidinyl, thiodiazolyl, oxadiazolyl, oxatriazolyl, dioxazolyl, oxathiazolyl, oxathiolyl, oxathiolanyl, pyranyl, tetrahydropyranyl, thiopyranyl, tetrahydrothiopyranyl, pyridinyl, piperidyl, diazinyl, piperazinyl, triazinyl, isooxazolyl, oxazolyl, oxazinyl, dihydrooxazinyl, oxathiazinyl, oxadiazinyl, morpholinyl, morpholino, thiomorpholinyl, thiomorpholino, azepinyl, hexahydroazepinyl, oxepinyl, thiepinyl, diazepinyl, tetrahydrodiazepinyl, pyridonyl, pyrimidinyl, hexahydropyrimidinyl, dioxanyl, thiiranyl, oxetanyl, azetidinyl, dioxolanyl, dioxolyl, and oxabicycloheptanyl.

Alternatively, a heterocyclyl moiety can be a polycyclic structure. Examples of polycyclic heterocyclyl include bridged, fused, and spirocyclic heterocyclyls. In a bridged heterocyclyl, the rings share at least two common non-adjacent atoms. In a fused-ring heterocyclyl, two or more rings (e.g., dicyclic heterocyclyl or tricyclic heterocyclyl) may be fused together, such that the two rings share one common bond. Examples of fused-ring heterocyclyl containing two or three rings include imidazopyrazinyl, imidazopyridinyl, imidazopyridazinyl, thiazolopyridinyl, indolizinyl, pyranopyrrolyl, purinyl, naphthyridinyl, pyridopyridinyl, pteridinyl, dihydrochromenyl, tetrahydroisoquinolinyl, indolyl, isoindolyl, indazolyl, indolinyl, isoindolinyl, isoindazolyl, benzazinyl, phthalazinyl, quinoxalinyl, quinazolinyl, quinolyl, isoquinolyl, cinnolinyl, benzodiazinyl, benzopyranyl, benzotriazolyl, benzimidazolyl, benzoxazolyl, benzoxadiazolyl, benzofuranyl, isobenzofuranyl, benzothienyl, benzoxazinyl, benzotriazolyl, benzisoxazinyl, benzisooxazolyl, thienopyridyl, thienopyrrolyl, thienopyrazolyl, thienopyrazinyl, furopyrrolyl, thienothienyl, imidazopyridyl, pyrazolopyridyl, thiazolopyridyl, pyrazolopyrimidinyl, pyrazolotrianizyl, pyridazolopyridyl, triazolopyridyl, imidazothiazolyl, pyrazinopyridazinyl, quinazolinyl, quinolyl, isoquinolyl, naphthyridinyl, dihydrothiazolopyrimidinyl, tetrahydroquinolyl, tetrahydroisoquinolyl, dihydrobenzofuryl, dihydrobenzoxazinyl, dihydrobenzimidazolyl, tetrahydrobenzothienyl, tetrahydrobenzofuryl, benzodioxolyl, benzodioxonyl, chromanyl, chromenyl, octahydrochromenyl, dihydrobenzodioxynyl, dihydrobenzooxezinyl, dihydrobenzodioxepinyl, dihydrothienodioxynyl, carbazolyl, acridinyl, xanthenyl, phenothiazinyl, phenoxathiinyl, phenoxazinyl, dibenzofuryl, imidazoquinolyl, and tetrahydrocarbazolyl. A typical fused-ring heterocyclyl is

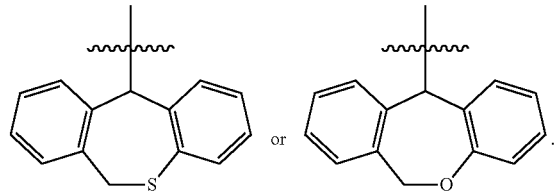

Compounds of Formula (I) include the following four classes of compounds, i.e., Classes I-IV.

The Class I compounds feature that $A_2$ is $NR_7$ and $A_3$ is $CR_5'R_6'$.

The Class II compounds feature that $A_2$ is $CR_5R_6$ and $A_3$ is $NR_7'$.

The Class III compounds feature that $A_2$ is $CR_5R_6$ and $A_3$ is $CR_5'R_6'$. In this class, $R_5$ and $R_5'$, together with the adjacent atom to which they are each attached, can form $C_{3-10}$ carbocyclyl or $C_{3-10}$ heterocyclyl.

The Class IV compounds feature that $A_2$ is $NR_7$ and $A_3$ is $NR_7'$.

Referring back to Formula (I), $R_1$ is typically hydrogen, deuterium, cyano, halogen, hydroxyl, $C_{1-6}$ alkyl, or $C_{1-6}$ alkoxy. For example, $R_1$ is hydrogen, deuterium or $C_{1-6}$ alkyl. An exemplary compound of Formula (I) has $R_1$ being hydrogen.

On the other hand, each of $R_4$, $R_5$, $R_5'$, $R_6$, and $R_6'$, independently, is typically hydrogen, deuterium, halogen, cyano, hydroxyl, $C_{1-6}$ alkyl, $C_{2-6}$ alkenyl, $C_{1-6}$ alkoxy, $C_{3-20}$ carbocyclyl, or $C_{3-20}$ heterocyclyl; and each of $R_7$ and $R_7'$, independently, is typically hydrogen, deuterium, carboxyl, $C_{1-6}$ alkyl, $C_{3-20}$ carbocyclyl, or $C_{3-20}$ heterocyclyl. For example, each of $R_7$ and $R_7'$, independently, is $C_{1-6}$ alkyl, $C_{3-20}$ carbocyclyl, or $C_{3-20}$ heterocyclyl, each of $C_{1-6}$ alkyl, $C_{3-20}$ carbocyclyl, and $C_{3-20}$ heterocyclyl being optionally substituted with 1 to 3 $C_{3-8}$ carbocyclyl or $C_{3-8}$ heterocyclyl. Other exemplary compounds of Formula (I) each have $R_7$ and $R_7'$, independently, being

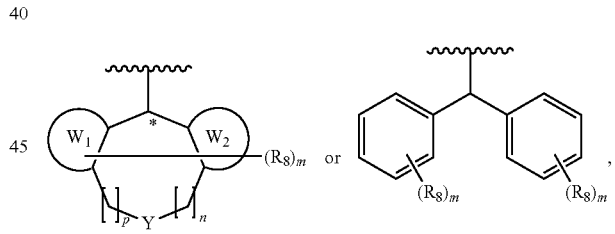

in which each of $W_1$ and $W_2$, independently, is $C_{3-8}$ carbocyclyl or $C_{3-8}$ heterocyclyl; Y is O, S, SO, $SO_2$, or $CH_2$; $R_8$ is hydrogen, deuterium, halogen, hydroxyl, $C_{1-6}$ alkyl, or $C_{1-6}$ alkoxy, $C_{1-6}$ alkyl or $C_{1-6}$ alkoxy being optionally substituted with 1 to 5 deuterium, halogen or hydroxyl groups; m is an integer of 1 to 5; n is an integer of 0 to 2; p is an integer of 0 to 2; and the star (*) indicates a chiral center. In one embodiment, each of $R_7$ and $R_7'$, independently, is

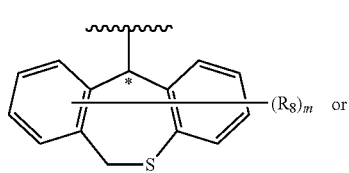

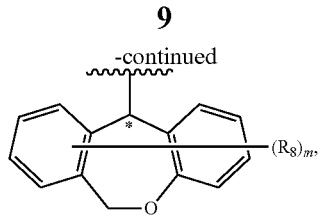

in which m is 1, 2, or 3. In one embodiment, each of $R_7$ and $R_7'$ is

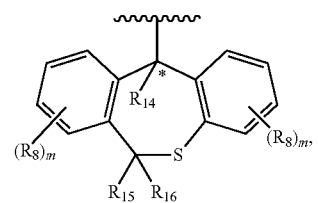

in which m is 1, 2, or 3; each of $R_{14}$, $R_{15}$ and $R_{16}$, independently, is hydrogen or deuterium.

In one embodiment, compounds of Formula (I) each have $A_2$ being $NR_7$ and $A_3$ being $CR_5'R_6'$, in which each of $R_5'$ and $R_6'$, independently, is hydrogen, deuterium, halogen, cyano, hydroxyl, $C_{1-6}$ alkyl, $C_{2-6}$ alkenyl, $C_{1-6}$ alkoxy, $C_{3-20}$ carbocyclyl, or $C_{3-20}$ heterocyclyl; and $R_7$ is hydrogen, deuterium, carboxyl, $C_{1-6}$ alkyl, $C_{3-20}$ carbocyclyl, or $C_{3-20}$ heterocyclyl. In one embodiment, $R_7$ is $C_{1-6}$ alkyl, $C_{3-20}$ carbocyclyl, or $C_{3-20}$ heterocyclyl, each of $C_{1-6}$ alkyl, $C_{3-20}$ carbocyclyl, and $C_{3-20}$ heterocyclyl being optionally substituted with 1 to 3 $C_{3-8}$ carbocyclyl or $C_{3-8}$ heterocyclyl. In another embodiment, $R_7$ is

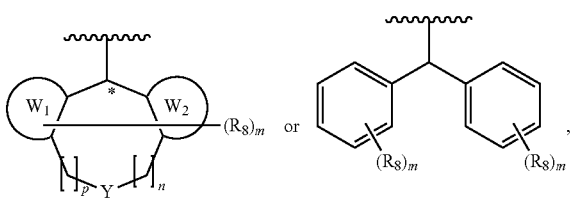

in which each variable is defined as set forth above. For example, $R_7$ is

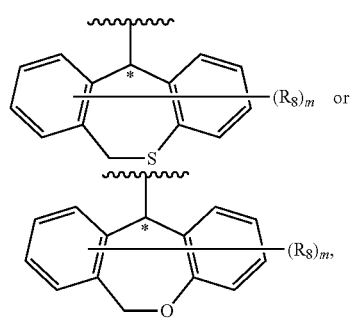

in which m is 1, 2, or 3.

In another embodiment, compounds of Formula (I) each have $A_2$ being $NR_7$ and $A_3$ being $CR_5'R_6'$, in which $R_1$ is hydrogen, deuterium, halogen, or $C_{1-6}$ alkyl; each of $R_2$, $R_2'$, $R_3$, and $R_3'$, independently, is hydrogen, deuterium, halogen, cyano, hydroxyl, carboxyl, amino, formyl, nitro, $C_{1-6}$ alkyl, $C_{2-6}$ alkenyl, $C_{2-6}$ alkynyl, $C_{1-6}$ alkoxy, $C_{2-6}$ alkenyloxy, $C_{1-6}$ alkylcarbonyl, $C_{1-6}$ alkyloxycarbonyl, $C_{1-6}$ alkylamine, $C_{3-20}$ carbocyclyl or $C_{3-20}$ heterocyclyl; each of $R_5'$ and $R_6'$, independently, is hydrogen, deuterium, halogen, $C_{1-6}$ alkyl, or $C_{2-6}$ alkenyl; and $R_7$ is hydrogen, deuterium, carboxyl, $C_{1-6}$ alkyl, $C_{3-20}$ carbocyclyl, or $C_{3-20}$ heterocyclyl. In another embodiment, $R_7$ is $C_{1-6}$ alkyl, $C_{3-20}$ carbocyclyl, or $C_{3-20}$ heterocyclyl, each of $C_{1-6}$ alkyl, $C_{3-20}$ carbocyclyl, and $C_{3-20}$ heterocyclyl being optionally substituted with 1 to 3 $C_{3-8}$ carbocyclyl or $C_{3-8}$ heterocyclyl. Exemplary compounds in this embodiment each have $R_7$ being

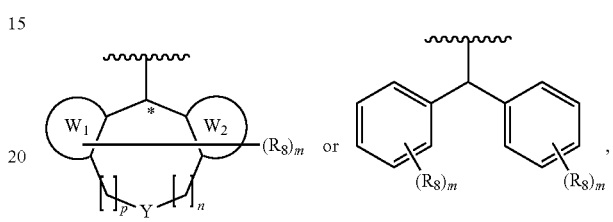

in which each variable is defined as set forth above. Examples of $R_7$ include, but are not limited to,

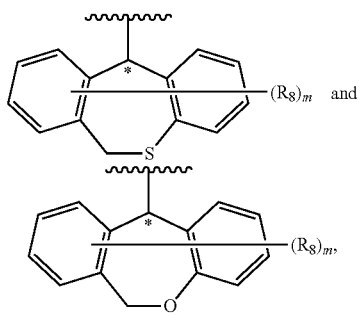

in which m is 1, 2, or 3.

In a further embodiment of compounds of Formula (I), $A_1$ is CH or N; $A_2$ is $NR_7$; $A_3$ is $CR_5'R_6'$; $R_1$ is hydrogen, deuterium or $C_{1-6}$ alkyl; each of $R_2$, $R_2'$, $R_3$, and $R_3'$, independently, is hydrogen, deuterium, halogen, cyano, hydroxyl, carboxyl, amino, formyl, nitro, $C_{1-6}$ alkyl, $C_{2-6}$ alkenyl, $C_{2-6}$ alkynyl, $C_{1-6}$ alkoxy, $C_{2-6}$ alkenyloxy, $C_{1-6}$ alkylcarbonyl, $C_{1-6}$ alkyloxycarbonyl, $C_{1-6}$ alkylamine, $C_{3-20}$ carbocyclyl or $C_{3-20}$ heterocyclyl; $R_5'$ is hydrogen; $R_6'$ is hydrogen, deuterium, $C_{1-6}$ alkyl, or $C_{2-6}$ alkenyl; and $R_7$ is

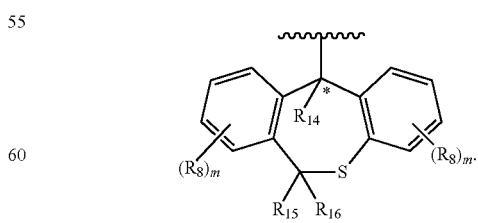

In one embodiment, the compounds of Formula (I) can be represented by the following formulas, i.e., Formula (II) and Formula (III):

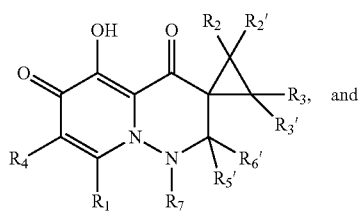
(II)

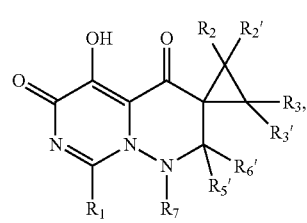
(III)

in which $R_1$, $R_2$, $R_2'$, $R_3$, $R_3'$, $R_4$, $R_5'$, $R_6'$, and $R_7$ are defined as above.

Each of the above-listed exemplary compounds of Formula (I) can be converted into a prodrug thereof having the following formula:

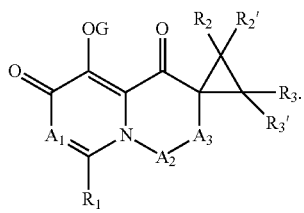

In this formula, G can be —C($R_9R_9'$)—O—CO—$R_{10}$, —C($R_9R_9'$)—O—CO—O—$R_{10}$, —C($R_9R_9'$)—$NR_{11}$—C(=O)—CO—O—$R_{10}$, —C($R_9R_9'$)—O—CO—C($R_9R_9'$)—$NR_{11}$—CO—O—$R_{10}$, —C($R_9R_9'$)—C($R_9R_9'$)—O—CO—$R_{10}$, —C($R_9R_9'$)—$R_{10}$, —C(=O)—O—$R_{10}$, —C(=O)—$R_{10}$, —C(=O)—O-alkylene-O—$R_{10}$, —C(=O)—$NR_{10}R_{11}$, or —P(=O)($R_{12}R_{13}$), in which each of $R_9$, $R_9'$, and $R_{11}$, independently, is hydrogen or $C_{1-8}$ alkyl; $R_{10}$ is $C_{1-8}$ alkyl, $C_{3-10}$ carbocyclyl, or $C_{3-10}$ heterocyclyl; $R_{12}$ is $C_{1-8}$ alkoxy; and $R_{13}$ is $C_{1-8}$ alkoxy or $C_{1-8}$ alkylamine. An exemplary G is one of the following groups:

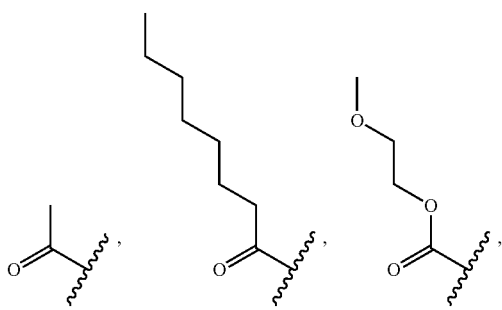

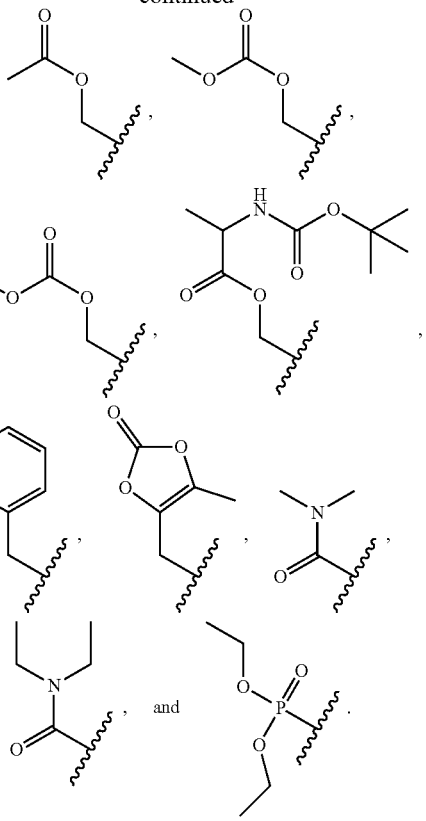

The —OG group is converted into an —OH group in the formula (I) by a decomposition reaction caused by drug-metabolizing enzymes, hydrolases, gastric acids, enterobacteria, etc. under physiological conditions in vivo. The prodrug becomes a parent compound having an inhibitory activity on cap-dependent endonuclease in vivo after administration thereof. In this disclosure, the prodrugs demonstrate better bioavailability and higher maximum concentration ($C_{max}$) than the parent compounds.

Compounds of this disclosure that have chiral centers may exist as stereoisomers. Stereoisomers of the compounds of Formula (I) can include cis and trans isomers, optical isomers such as (R) and (S) enantiomers, diastereomers, geometric isomers, rotational isomers, atropisomers, conformational isomers, and tautomers of the compounds, including compounds exhibiting more than one type of isomerism and mixtures thereof (such as racemates and diastereomers). All such isomeric forms are contemplated. In addition, the compounds of Formula (I) in the present disclosure may exhibit the phenomena of tautomerism.

Of note, the compounds of Formula (I) with enriched enantiopurity can have an enantiomeric excess of 90% or higher (e.g., ≥95% and ≥99%).

Also within this disclosure is a pharmaceutical composition containing one or more of the above-described compounds, salts, metabolites or prodrugs for treating influenza.

Further covered by this disclosure is a method for treating influenza, the method including administering to a subject in need thereof an effective amount of a compound of Formula (I), or a pharmaceutically acceptable salt, metabolite or prodrug thereof.

Still within the scope of this disclosure is a method of preparing a compound of Formula (I) below, or a pharmaceutically acceptable salt, metabolite, or prodrug thereof,

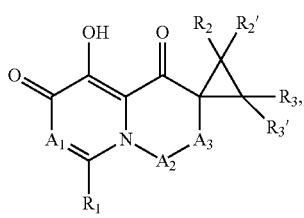

(I)

wherein the method includes the following steps: (i) providing an aldehyde

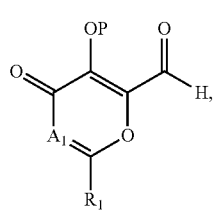

P being a protecting group; (ii) reacting the aldehyde with a carbonyl compound

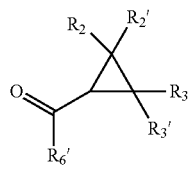

to afford a first intermediate

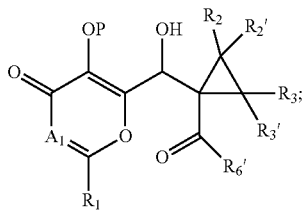

(iii) reacting the first intermediate with a hydrazine to afford a second intermediate

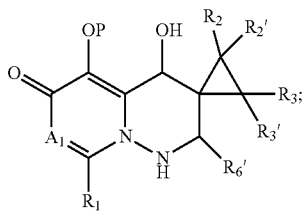

and (iv) converting the second intermediate to a compound of Formula (I), or a pharmaceutically acceptable salt or prodrug thereof, in which $A_1$ is $CR_4$, $A_2$ is $NR_7$, and $A_3$ is $CR_5'R_6'$; $R_1$ is hydrogen, deuterium, halogen, cyano, hydroxyl, carboxyl, amino, $C_{1-6}$ alkyl, $C_{2-6}$ alkenyl, $C_{2-6}$ alkynyl, $C_{1-6}$ alkoxy, $C_{1-6}$ alkylamine, $C_{3-20}$ carbocyclyl, or $C_{3-20}$ heterocyclyl; each of $R_2$, $R_2'$, $R_3$, and $R_3'$, independently, is hydrogen, deuterium, halogen, cyano, hydroxyl, carboxyl, amino, formyl, nitro, $C_{1-6}$ alkyl, $C_{2-6}$ alkenyl, $C_{2-6}$ alkynyl, $C_{1-6}$ alkoxy, $C_{2-6}$ alkenyloxy, $C_{1-6}$ alkylcarbonyl, $C_{1-6}$ alkyloxycarbonyl, $C_{1-6}$ alkylamine, $C_{3-20}$ carbocyclyl, or $C_{3-20}$ heterocyclyl; $R_4$ is hydrogen, deuterium, halogen, cyano, hydroxyl, carboxyl, amino, $C_{1-6}$ alkyl, $C_{2-6}$ alkenyl, $C_{2-6}$ alkynyl, $C_{1-6}$ alkoxy, $C_{3-20}$ carbocyclyl, or $C_{3-20}$ heterocyclyl; $R_5'$ is H; and each of $R_6'$ and $R_7$, independently, is hydrogen, deuterium, halogen, cyano, hydroxyl, carboxyl, $C_{1-6}$ alkyl, $C_{2-6}$ alkenyl, $C_{2-6}$ alkynyl, $C_{1-6}$ alkoxy, $C_{3-20}$ carbocyclyl, or $C_{3-20}$ heterocyclyl. Again, each of the $C_{1-6}$ alkyl, $C_{2-6}$ alkenyl, $C_{2-6}$ alkynyl, $C_{1-6}$ alkoxy, $C_{2-6}$ alkenyloxy, $C_{1-6}$ alkylcarbonyl, $C_{1-6}$ alkyloxycarbonyl, $C_{1-6}$ alkylamine, $C_{3-20}$ carbocyclyl, and $C_{3-20}$ heterocyclyl is optionally substituted with 1 to 5 moieties of deuterium, halogen, hydroxyl, cyano, amino, nitro, carboxyl, $C_{1-6}$ alkyl, $C_{1-6}$ alkoxy, $C_{1-6}$ alkylamino, $C_{1-6}$ alkyl($C_{3-10}$ carbocyclyl), $C_{1-6}$ alkyl($C_{3-10}$ heterocyclyl), $C_{1-6}$ alkoxy($C_{3-10}$ carbocyclyl), $C_{1-6}$ alkoxy($C_{3-10}$ heterocyclyl), $C_{3-10}$ carbocyclyl, or $C_{3-10}$ heterocyclyl.

The compounds of Formula (I) described above can be initially screened using in vitro assays, e.g., the cytopathic effect reduction assay described in EXAMPLE 2 below, for their potency in inhibiting the activity of cap-dependent endonuclease. They can be subsequently evaluated using in vivo assays, e.g., the influenza A mouse model study described in EXAMPLE 3 below. The selected compounds can be further tested to verify their efficacy in treating influenza. Based on the results, appropriate dosage ranges and administration routes can be investigated and determined.

Without further elaboration, it is believed that one skilled in the art can, based on the above description, utilize the present disclosure to its fullest extent. The following specific examples, i.e., EXAMPLES 1-3, are therefore to be construed as merely illustrative, and not limitative of the remainder of the disclosure in any way whatsoever.

Among the specific examples, EXAMPLE 1 sets forth the procedures for preparing certain intermediates, exemplary compounds of Formula (I), and exemplary prodrugs of compounds of Formula (I), as well as the analytical data for the compounds thus prepared; and EXAMPLES 2 and 3 set forth the protocols for testing these compounds.

Shown in the table below are the structures of 39 exemplary compounds of Formula (I).

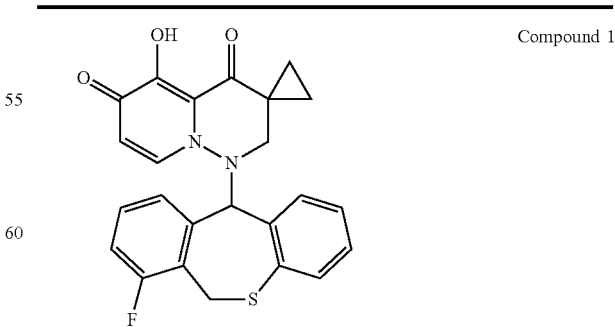

Compound 1

15
-continued
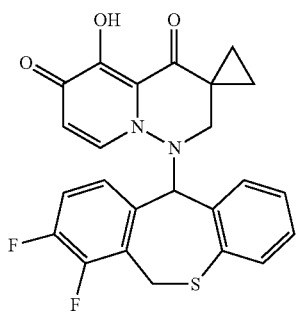
Compound 2
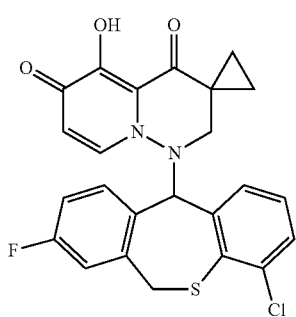 [SMILES: O=C1c2c(O)c(=O)ccn2N(C2c3ccc(F)cc3CSc3c(Cl)cccc32)CC12CC2]
Compound 3
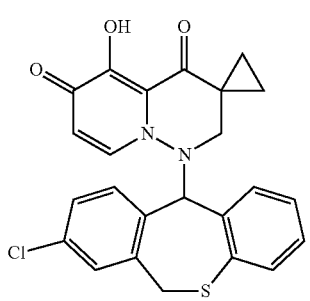 [SMILES: O=C1c2c(O)c(=O)ccn2N(C2c3ccc(Cl)cc3CSc3ccccc32)CC12CC2]
Compound 4
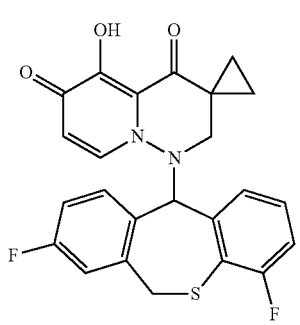 [SMILES: O=C1c2c(O)c(=O)ccn2N(C2c3ccc(F)cc3CSc3c(F)cccc32)CC12CC2]
Compound 5
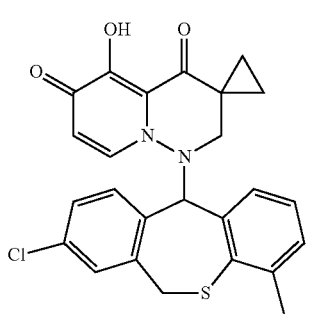 [SMILES: Cc1cccc2c1SCc1cc(Cl)ccc1C2N1CC2(CC2)C(=O)c2c(O)c(=O)ccn21]
Compound 6
16
-continued
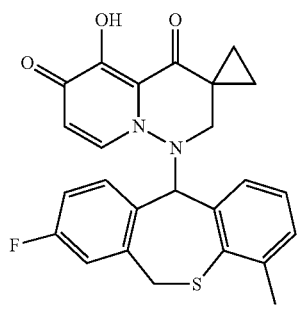 [SMILES: Cc1cccc2c1SCc1cc(F)ccc1C2N1CC2(CC2)C(=O)c2c(O)c(=O)ccn21]
Compound 7
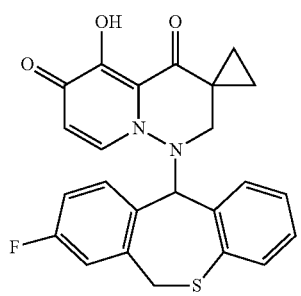 [SMILES: O=C1c2c(O)c(=O)ccn2N(C2c3ccc(F)cc3CSc3ccccc32)CC12CC2]
Compound 8
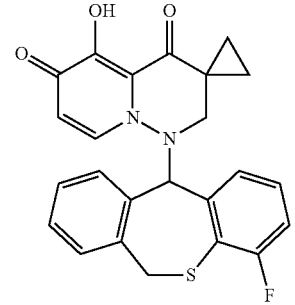 [SMILES: O=C1c2c(O)c(=O)ccn2N(C2c3ccccc3CSc3c(F)cccc32)CC12CC2]
Compound 9
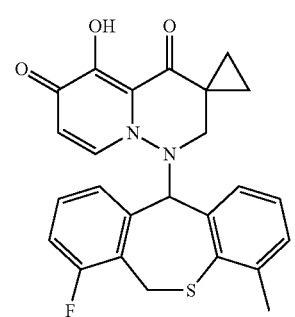 [SMILES: Cc1cccc2c1SCc1c(F)cccc1C2N1CC2(CC2)C(=O)c2c(O)c(=O)ccn21]
Compound 10
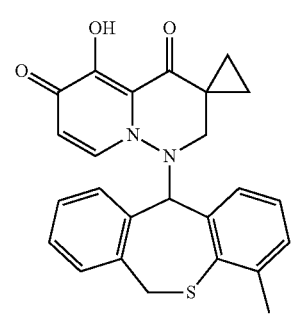 [SMILES: Cc1cccc2c1SCc1ccccc1C2N1CC2(CC2)C(=O)c2c(O)c(=O)ccn21]
Compound 11

| | |
|---|---|
| 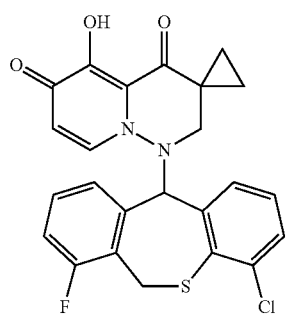 [SMILES: O=C1c2c(O)c(=O)ccn2N(C2c3cccc(F)c3CSc3c(Cl)cccc32)CC12CC2] Compound 12 | 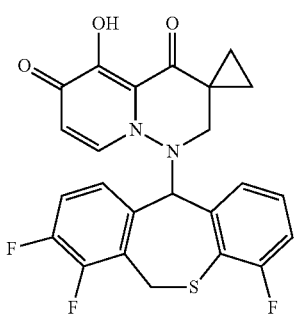 [SMILES: Cc1cccc2c1SCc1c(ccc(F)c1F)C2N1CC2(CC2)C(=O)c2c(O)c(=O)ccn21] Compound 17 |
| 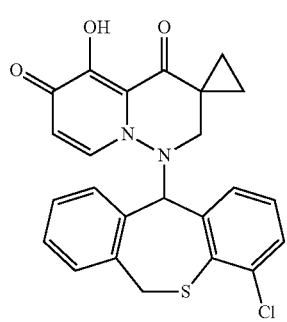 Compound 13 | 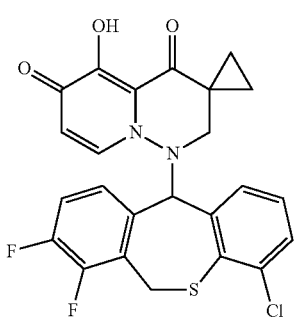 [SMILES: O=C1c2c(O)c(=O)ccn2N(C2c3ccc(F)c(F)c3CSc3c(Cl)cccc32)CC12CC2] Compound 18 |
| 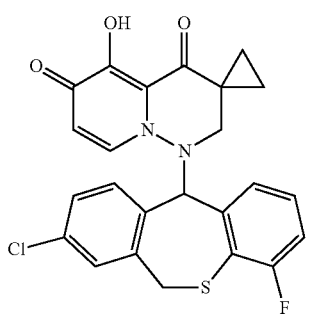 Compound 14 | 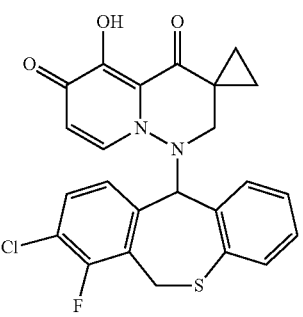 [SMILES: O=C1c2c(O)c(=O)ccn2N(C2c3ccccc3SCc3c2ccc(Cl)c3F)CC12CC2] Compound 19 |
| 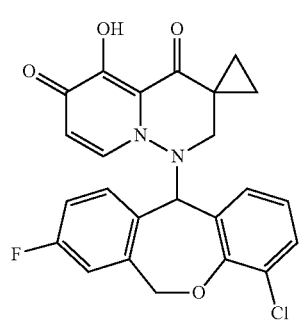 Compound 15 | 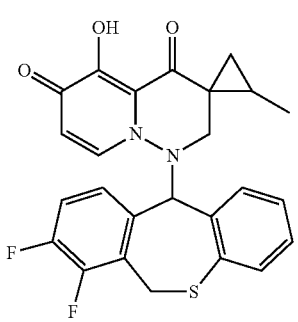 [SMILES: CC1CC12CN(C1c3ccccc3SCc3c1ccc(F)c3F)n1ccc(=O)c(O)c1C2=O] Compound 20 |
| 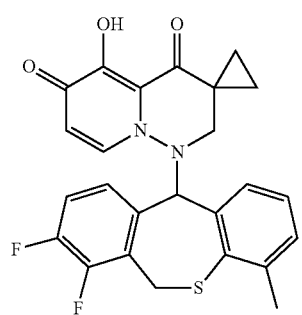 Compound 16 | 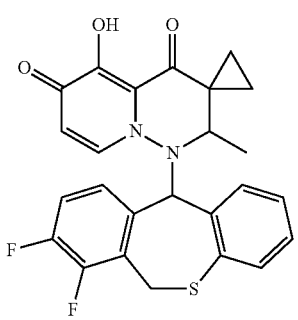 [SMILES: CC1N(C2c3ccccc3SCc3c2ccc(F)c3F)n2ccc(=O)c(O)c2C(=O)C12CC2] Compound 21 |

-continued
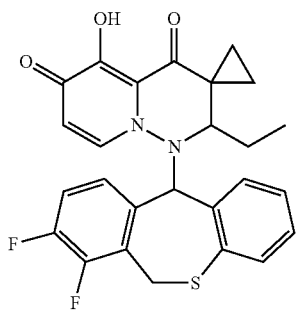 [SMILES: CCC1N(C2c3ccccc3SCc3c2ccc(F)c3F)n2ccc(=O)c(O)c2C(=O)C12CC2]
Compound 22
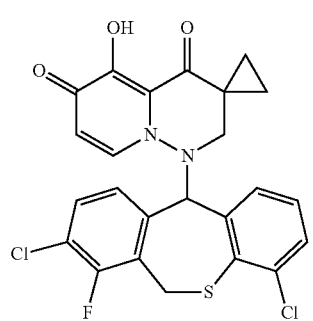 [SMILES: O=C1c2c(O)c(=O)ccn2N(C2c3ccc(Cl)c(F)c3CSc3c(Cl)cccc32)CC12CC2]
Compound 23
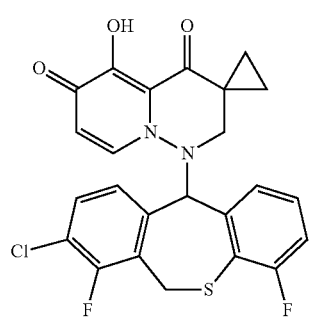
Compound 24
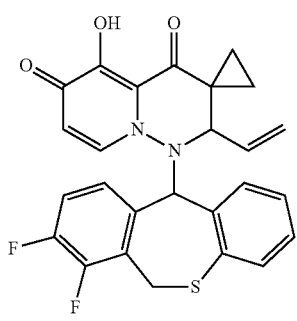 [SMILES: C=CC1N(C2c3ccccc3SCc3c2ccc(F)c3F)n2ccc(=O)c(O)c2C(=O)C12CC2]
Compound 25
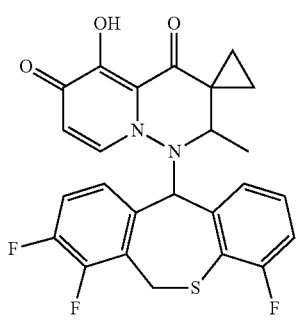 [SMILES: CC1N(C2c3ccc(F)c(F)c3CSc3c(F)cccc32)n2ccc(=O)c(O)c2C(=O)C12CC2]
Compound 26
-continued
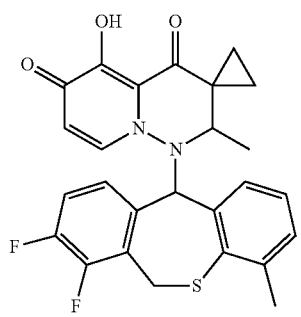 [SMILES: Cc1cccc2c1SCc1c(ccc(F)c1F)C2N1C(C)C2(CC2)C(=O)c2c(O)c(=O)ccn21]
Compound 27
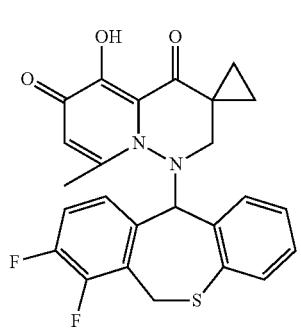 [SMILES: Cc1cc(=O)c(O)c2n1N(C1c3ccccc3SCc3c1ccc(F)c3F)CC1(CC1)C2=O]
Compound 28
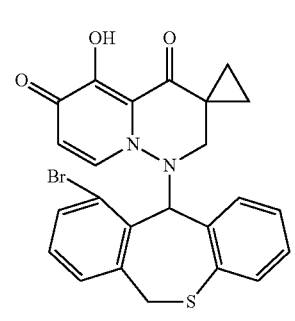 [SMILES: O=C1c2c(O)c(=O)ccn2N(C2c3ccccc3SCc3cccc(Br)c32)CC12CC2]
Compound 29
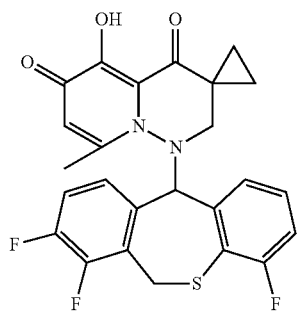
Compound 30
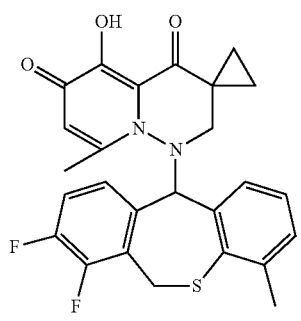 [SMILES: Cc1cccc2c1SCc1c(ccc(F)c1F)C2N1CC2(CC2)C(=O)c2c(O)c(=O)cc(C)n21]
Compound 31

Compound 32
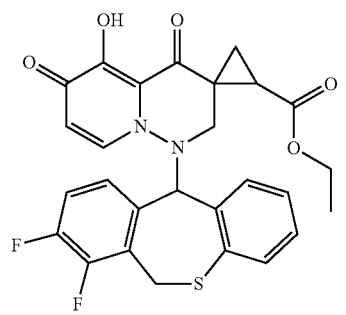 [SMILES: CCOC(=O)C1CC12CN(C1c3ccccc3SCc3c1ccc(F)c3F)n1ccc(=O)c(O)c1C2=O]

Compound 33
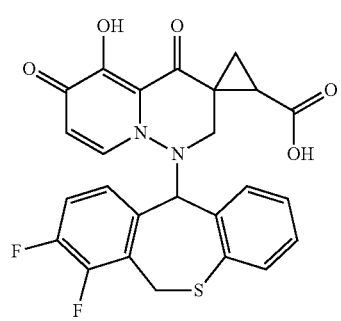 [SMILES: O=C(O)C1CC12CN(C1c3ccccc3SCc3c1ccc(F)c3F)n1ccc(=O)c(O)c1C2=O]

Compound 34
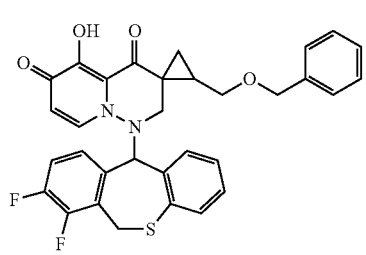 [SMILES: O=C1c2c(O)c(=O)ccn2N(C2c3ccccc3SCc3c2ccc(F)c3F)CC12CC2COCc1ccccc1]

Compound 35
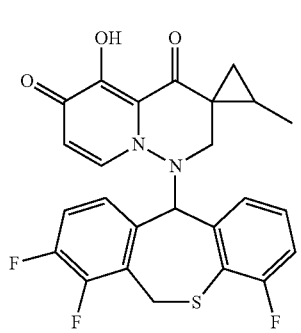

Compound 36
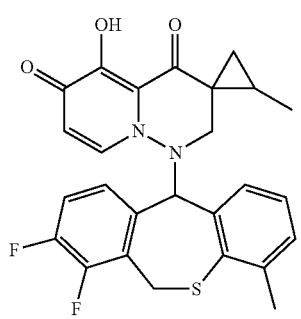 [SMILES: Cc1cccc2c1SCc1c(ccc(F)c1F)C2N1CC2(CC2C)C(=O)c2c(O)c(=O)ccn21]

Compound 37
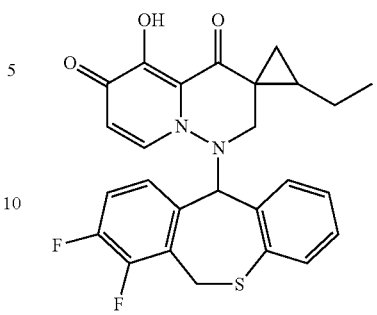

Compound 38
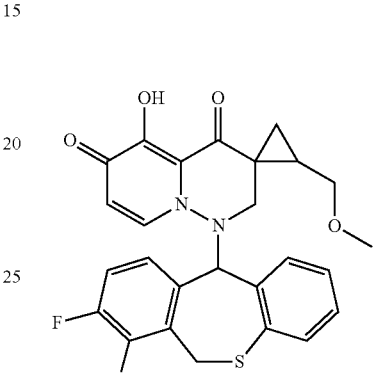

Compound 39
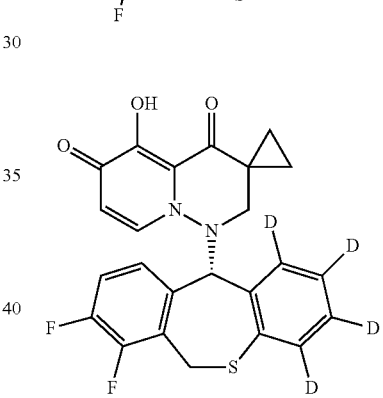

Described below are the procedures used to synthesize the above-described 39 exemplary compounds.

All the reagents and solvents were purchased from commercial sources and used without further purification unless otherwise indication. All the reactions were carried out under dry nitrogen or argon atmosphere and monitored by thin layer chromatography (TLC) using Merck Silica gel 60 $F_{254}$ glass-backed plate. Column chromatography was performed by Merck Silica gel 60 (0.040-0.063 mm, 230-400 mesh). $^1$H NMR and $^{13}$C NMR spectra were measured by Varian Mercury-300 and Varian Bruker AVIII-500 spectrometers, and the chemical shifts (δ) were reported in parts per million (ppm) relative to the resonance of the solvent peak. Multiplicities are reported with the following abbreviations: s (singlet), d (doublet), t (triplet), q (quartet), quin (quintet), m (multiplet), or br (broad). Low-resolution mass spectra were measured by HP Hewlett Packard 1100 series.

The following scheme was followed for synthesizing certain compounds of Formula (I).

23

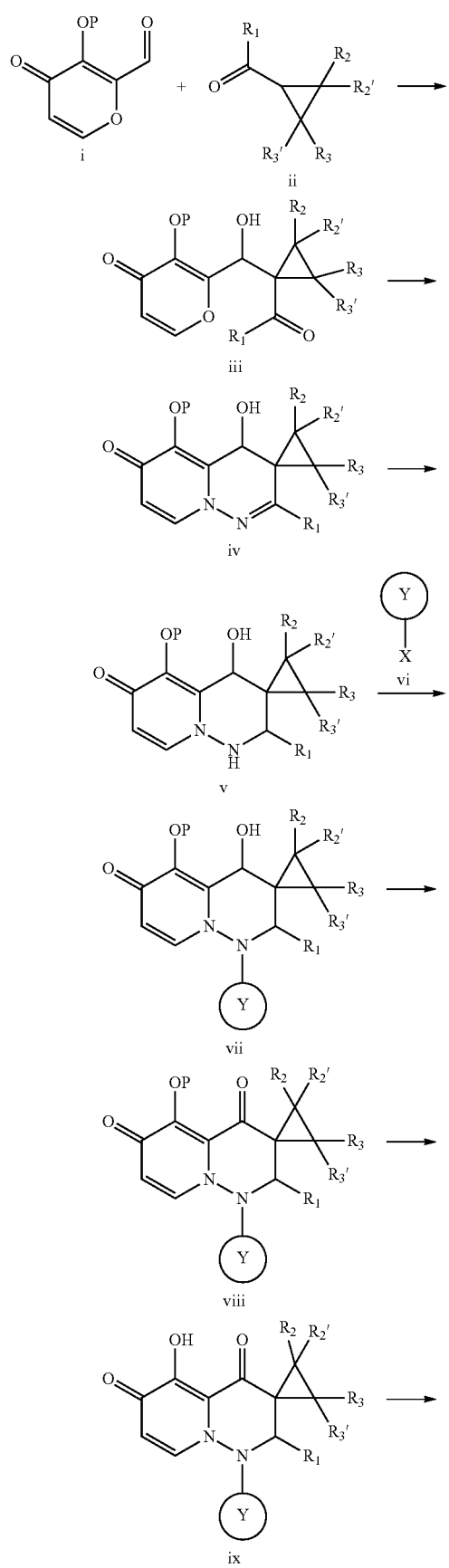

24

-continued

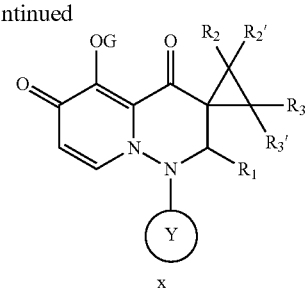

x

EXAMPLE 1

Preparation and Characterization of Compounds 1-39

Synthesis and Characterization of Compound 1

1-(1-Fluoro-5,11-dihydro-10-thia-dibenzo[a,d]cyclohepten-5-yl)-5-hydroxy-3,3-cyclopropyl-2,3-dihydro-1H-pyrido[1,2-b]pyridazine-4,6-dione (Compound 1)

Compound I-3 was first prepared from commercially available 3-benzyloxy-4-oxo-4H-pyran-2-carbaldehyde via intermediates I-1 and 1-2, following the scheme shown below:

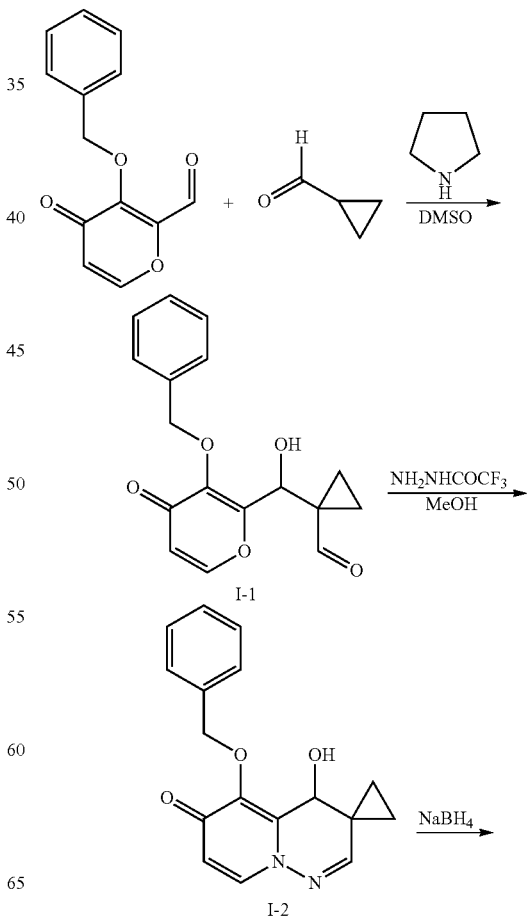

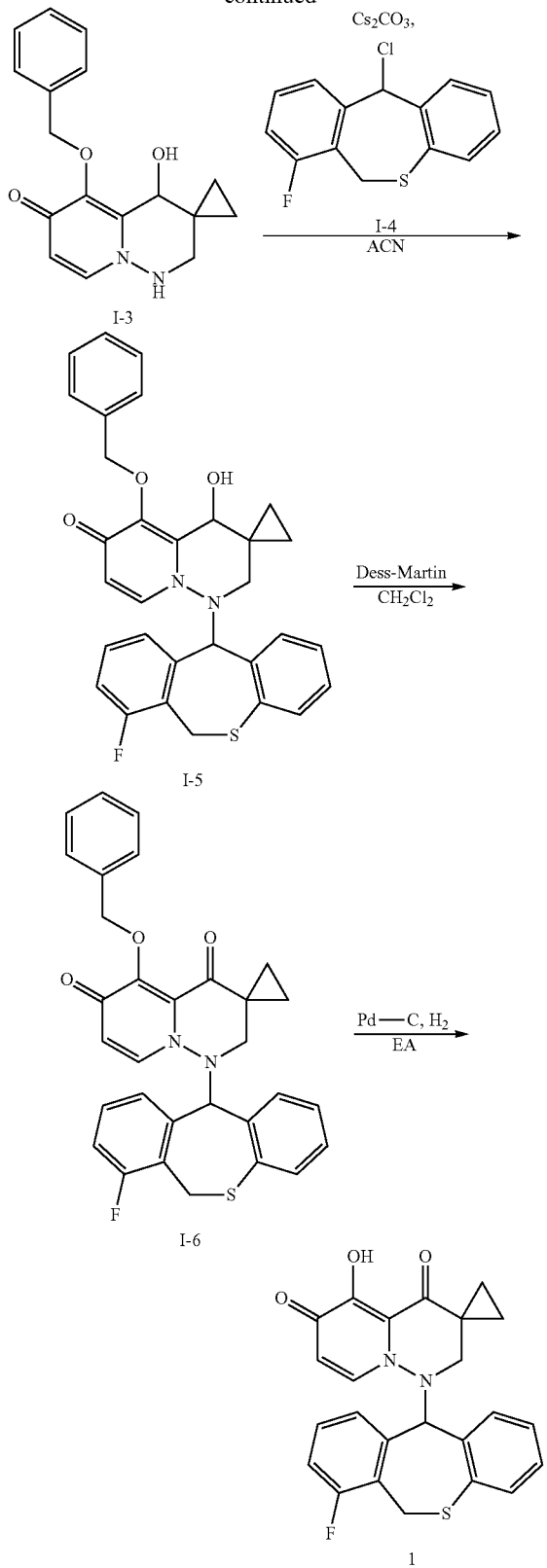

at 50° C. for 23 to 24 hours and then cooled to room temperature. The resulting mixture was dissolved in CH$_2$Cl$_2$ (1.0 L), washed with 1N HCl$_{(aq)}$ (1.0 L) and a saturated aqueous solution of NaHCO$_3$ (1.0 L), followed by a saturated brine (1.0 L). The organic phase was separated and dried over anhydrous MgSO$_4$. The solvent was removed under reduced pressure to obtain residue (133 g). The residue thus obtained was dissolved in EtOAc (1.0 L), washed with a saturated aqueous solution of NaHCO$_3$ (1.0 L), followed by a saturated aqueous solution of NaCl (1.0 L), and dried over anhydrous MgSO$_4$, and then the solvent was evaporated under reduced pressure to form a black crude material (106 g). The resulting crude material was purified by column chromatography (hexane/EtOAc=7/3) and then recrystallization with (hexane/EtOAc=1/1) to afford compound I-1 as a yellow-green solid (87 g, 66%).

NH$_2$NHCOCF$_3$ (8.23 g, 64 mmole) was added to the solution of compound I-1 (9.65 g, 32 mmole) in MeOH (145 mL) and H$_2$O (73 mL). The reaction mixture was stirred at 50° C. for 20 hours. After cooling to room temperature, the solvent were removed under reduced pressure. The solid residue was dissolved in CH$_2$Cl$_2$ (500 mL×3) and washed with a saturated aqueous solution of NaCl (200 mL). The organic phase was separated and dried over anhydrous MgSO$_4$. The solvent was removed under reduced pressure and the crude product was washed with MTBE (250 mL) to afford the compound I-2 (8.6 g, 90%).

The NaBH$_4$ (1.05 g, 27.8 mmole) was added slowly to a solution of compound I-2 (4.32 g, 13.9 mmole) in MeOH (38 mL) at 0° C. The reaction mixture was stirred at room temperature for 1 hour. After 1 hour, H$_2$O (10 mL) was added to the reaction solution, and the solvent was removed under reduced pressure. The solid residue was dissolved in CH$_2$Cl$_2$ (250 mL×3) and washed with a saturated aqueous solution of NaCl (100 mL). The organic phase was separated and dried over anhydrous MgSO$_4$, and removed under reduced pressure to obtain the crude product (4.47 g).

Compound I-4 was prepared from commercially available 9-fluoro-11H-10-thia-dibenzo[a,d]cyclohepten-5-one via the route shown below:

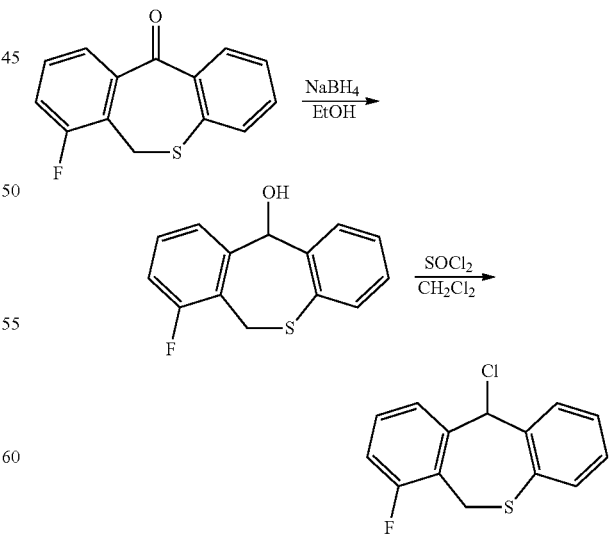

To a solution of 9-fluoro-11H-10-thia-dibenzo[a,d]cyclohepten-5-one (1.4 g, 6.1 mmole), NaBH$_4$ (0.28 g, 7.3

Pyrrolidine (30.9 g, 434 mmole) was added to the solution of 3-(benzyloxy)-4-oxo-4H-pyran-2-carbaldehyde (100 g, 434 mmole) and cyclopropanecarbaldehyde (91.3 g, 1.30 mmole) in solvent DMSO (1 L), and the mixture was stirred mmole) was stirred in THF/MeOH (1:1, 20 mL) at 0° C., then allowed to return to room temperature for 1 hour. After reaction completed, then quenched with H$_2$O and extracted with CH$_2$Cl$_2$, the organic layer was dried with Na$_2$SO$_4$ and concentrated under reduced pressure to obtain 1.4 g of crude residue, which was used in the next step without being purified. Then, the crude residue and SOCl$_2$ (0.88 ml, 12.2 mmole) were stirred in CH$_2$Cl$_2$ (10 mL) at 0° C., and then allowed to return to room temperature. After reaction completed and then concentrated under reduced pressure, crude compound I-4 was obtained which was directly used without being purified.

Compound 1 was prepared via intermediates I-3 to I-6 as follows. A solution of compound I-3 (150 mg, 0.5 mmole), cesium carbonate (491 mg, 1.5 mmole) and compound I-4 (265 mg, 1.0 mmole) was stirred in ACN (6 ml) at 50° C. for 3 hours. CHCl$_2$ dilute, H$_2$O wash, the organic layer Na$_2$SO$_4$ dried, concentrated under reduced pressure, the residue was purified by silica gel chromatography eluting with CH$_2$Cl$_2$:MeOH=39:1 to afford compound I-5 (92 mg, 0.17 mmole, yield: 34%).

To a solution of compound I-5 (92 mg, 0.17 mmole), Dess-Martin periodinane (1.09 g, 2.56 mmole) and NaHCO$_3$ (725 mg) were stirred in ACN (50 ml) at 75° C. for 1 hour. The reaction was washed with H$_2$O, and the organic layer Na$_2$SO$_4$ was dried and concentrated under reduced pressure. The residue was purified by silica gel chromatography eluting with CH$_2$Cl$_2$:MeOH=39:1 to afford compound I-6 (60 mg, 0.11 mmole, yield: 67%).

To a solution of compound I-6 (60 mg, 0.114 mmole) was dissolved in EA (20 ml) and CHCl$_2$ (10 ml), and Pd—C (35 mg) was added. The mixture was stirred under hydrogen (1 atm) at room temperature for 1 hour. The catalyst was removed by filtrating through a pad of celite. The filtrate was concentrated under reduced pressure to give compound 1 (46 mg, 0.106 mmole, yield: 93%). MS: m/z 435.1 (M+H)$^{30}$; $^1$H NMR (CDCl$_3$) δ7.31-6.89 (m, 6H), 6.66-6.64 (m, 1H), 6.57 (d, 1H), 5.83 (d, 1H), 5.42 (d, 1H), 5.02 (s, 1H), 4.14 (d, 1H), 4.06 (d, 1H), 3.32 (br, 1H), 2.91 (d, 1H), 1.88-1.86 (m, 1H), 1.70-1.68 (m, 1H), 0.99-0.96 (m, 1H), 0.84-0.79 (m, 1H).

Synthesis and Characterization of Compounds 2-39

Each of Compounds 2-39 was similarly prepared following the scheme as set forth above and the protocols described in the preparation of Compound 1.

Analytical data of compounds 2-39 are listed below.

Compound 2: MS: m/z 453.1 (M+H)$^+$; $^1$H NMR (CDCl$_3$) δ7.27 (d, 1H), 7.08-7.00 (m, 4H), 6.80-6.78 (m, 1H), 6.63 (d, 1H), 5.83 (d, 1H), 5.50 (dd, 1H), 5.23 (s, 1H), 4.15 (d, 1H), 4.06 (d, 1H), 2.91 (d, 1H), 2.43 (br, 1H), 1.92-1.84 (m, 1H), 1.78-1.67 (m, 1H), 0.96-0.92 (m, 1H), 0.86-0.81 (m, 1H).

Compound 3: MS: m/z 468.9 (M+H)$^+$; $^1$H NMR (CDCl$_3$) δ7.31-7.19 (m, 3H), 7.07-6.96 (m, 2H), 6.79-6.74 (m, 1H), 6.62 (d, 1H), 5.89-5.81 (m, 2H), 5.30 (s, 1H), 4.13 (d, 1H), 3.62 (d, 1H), 2.9 (d, 1H), 1.90-1.87 (m, 1H), 1.72-1.67 (m, 1H), 0.94-0.80 (m, 2H).

Compound 4: MS: m/z 451.1 (M+H)$^+$; $^1$H NMR (CDCl$_3$) δ7.31-7.08 (m, 6H), 6.80-6.78 (m, 1H), 6.65 (d, 1H), 5.83 (d, 1H), 5.71 (d, 1H), 5.21 (s, 1H), 4.13 (d, 1H), 3.51 (d, 1H), 2.89 (d, 1H), 1.89-1.87 (m, 1H), 1.71-1.69 (m, 1H), 0.97-0.83 (m, 2H).

Compound 5: MS: m/z 453.1 (M+H)$^+$; $^1$H NMR (CD$_3$OD) δ7.52-7.44 (m, 2H), 7.22-7.18 (m, 1H), 7.08-7.03 (m, 1H), 6.99-6.93 (m, 1H), 6.85-6.83 (m, 1H), 6.70-6.68 (m, 1H), 5.91 (d, 1H), 5.85 (d, 1H), 5.55 (s, 1H), 4.20 (d, 1H), 3.79 (d, 1H), 2.97 (d, 1H), 1.98-1.85 (m, 1H), 1.64-1.48 (m, 1H), 1.15-1.00 (m, 1H), 0.99-0.85 (m, 1H).

Compound 6: MS: m/z 465.1 (M+H)$^+$; $^1$H NMR (CDCl$_3$) δ7.31-7.10 (m, 4H), 7.00 (d, 1H), 6.74-6.69 (m, 1H), 6.53 (d, 1H), 5.82 (d, 1H), 5.75 (d, 1H), 5.23 (s, 1H), 4.13 (d, 1H), 3.61 (d, 1H), 2.90 (d, 1H), 2.25 (s, 3H), 1.89 (br, 1H), 1.72-1.70 (m, 1H), 1.62-1.60 (m, 1H), 0.97-0.93 (m, 1H), 0.85-0.82 (m, 1H).

Compound 7: MS: m/z 449.1 (M+H)$^+$; $^1$H NMR (CDCl$_3$) δ7.25-7.18 (m, 2H), 7.09-6.92 (m, 3H), 6.70 (t, 1H), 6.52 (d, 1H), 5.84-5.74 (m, 2H), 5.23 (s, 1H), 4.12 (d, 1H), 3.59 (d, 1H), 3.26 (br, 1H), 2.89 (d, 1H), 2.24 (s, 3H), 1.90-1.86 (m, 1H), 1.71-1.65 (m, 1H), 0.99-0.92 (m, 1H), 0.86-0.79 (m, 1H).

Compound 8: MS: m/z 435.1 (M+H)$^+$; $^1$H NMR (CDCl$_3$) δ7.29-7.18 (m, 2H), 7.07-6.94 (m, 4H), 6.80-6.76 (m, 1H), 6.65 (d, 1H), 5.84 (d, 1H), 5.75 (d, 1H), 5.21 (s, 1H), 4.15-4.01 (m, 1H), 3.50 (d, 1H), 2.91 (d, 1H), 1.89-1.87 (m, 1H), 1.72-1.67 (m, 1H), 0.97-0.93 (m, 1H), 0.87-0.80 (m, 1H).

Compound 9: MS: m/z 435.1 (M+H)$^+$; $^1$H NMR (DMSO-d$_6$) δ7.47-7.29 (m, 5H), 7.04-7.00 (m, 1H), 6.88-6.74 (m, 1H), 6.75-6.64 (m, 1H), 5.83 (d, 1H), 5.73 (d, 1H), 5.49 (s, 1H), 4.09-3.95 (m, 2H), 2.78 (d, 1H), 1.64-1.58 (m, 1H), 1.21-1.13 (m, 1H), 0.71-0.60 (m, 1H), 0.58-0.45 (m, 1H).

Compound 10: MS: m/z 449.1 (M+H)$^+$; $^1$H NMR (CD$_3$OD) δ7.47-7.45 (m, 1H), 7.28-7.18 (m, 3H), 7.04-7.02 (m, 1H), 6.73-6.70 (m, 2H), 5.84 (d, 1H), 5.58 (d, 1H), 5.49 (s, 1H), 4.18 (d, 2H), 2.98 (d, 1H), 2.24 (s, 3H), 1.98-1.87 (m, 1H), 1.67-1.58 (m, 1H), 1.18-1.03 (m, 1H), 0.96-0.87 (m, 1H).

Compound 11: MS: m/z 431.2 (M+H)$^+$; $^1$H NMR (CDCl$_3$) δ7.36-7.23 (m, 5H), 6.98 (d, 1H), 6.72-6.67 (m, 1H), 6.54 (d, 1H), 5.82 (d, 1H), 5.75 (d, 1H), 5.23 (s, 1H), 4.12 (d, 1H), 3.66 (d, 1H), 2.90 (d, 1H), 2.23 (s, 3H), 1.90-1.83 (m, 1H), 1.72-1.62 (m, 1H), 1.01-0.92 (m, 1H), 0.86-0.79 (m, 1H).

Compound 12: MS: m/z 469.1 (M+H)$^+$; $^1$H NMR (CDCl$_3$) δ7.26-7.02 (m, 5H), 6.76 (t, 1H), 6.63 (d, 1H), 5.89 (d, 1H), 5.51 (d, 1H), 5.32 (s, 1H), 4.17 (d, 1H), 4.15 (d, 1H), 3.17 (br, 1H), 2.91 (d, 1H), 1.93-1.87 (m, 1H), 1.72-1.67 (m, 1H), 1.00-0.81 (m, 2H).

Compound 13: MS: m/z 451.1 (M+H)$^+$; $^1$H NMR (CDCl$_3$) δ7.43-7.15 (m, 6H), 6.75 (t, 1H), 6.63 (d, 1H), 5.88 (d, 1H), 5.79 (d, 1H), 5.27 (s, 1H), 4.12 (d, 1H), 3.68 (d, 1H), 3.43 (br, 1H), 2.90 (d, 1H), 1.91-1.87 (m, 1H), 1.71-1.66 (m, 1H), 0.99-0.79 (m, 2H).

Compound 14: MS: m/z 469.1 (M+H)$^+$; $^1$H NMR (CDCl$_3$) δ7.38-7.16 (m, 4H), 6.94-6.88 (m, 1H), 6.83-6.76 (m, 1H), 6.50 (d, 1H), 5.72 (d, 1H), 5.75 (d, 1H), 5.26 (s, 1H), 4.14 (d, 1H), 3.60 (d, 1H), 2.90 (d, 1H), 2.60 (br, 1H), 1.90-1.88 (m, 1H), 1.71-1.69 (m, 1H), 0.96-0.81 (m, 2H).

Compound 15: MS: m/z 453.1 (M+H)$^+$; $^1$H NMR (CD$_3$OD) δ7.48-7.24 (m, 2H), 7.24-6.96 (m, 3H), 6.80-6.50 (m, 2H), 6.50-6.34 (m, 1H), 5.89 (d, 1H), 5.14-5.00 (m, 2H), 4.06 (d, 1H), 2.83 (d, 1H), 2.10-1.96 (m, 1H), 1.78-1.60 (m, 1H), 1.16-1.00 (m, 1H), 0.96-0.80 (m, 1H).

Compound 16: MS: m/z 467.1 (M+H)$^+$; $^1$H NMR (CDCl$_3$) δ7.21 (d, 1H), 7.10-7.00 (m, 3H), 6.72 (t, 1H), 6.51 (d, 1H), 5.82 (d, 1H), 5.51 (d, 1H), 5.24 (s, 1H), 4.16-4.07 (m, 2H), 2.91 (d, 1H), 2.24 (s, 3H), 2.03-1.66 (m, 3H), 0.99-0.81 (m, 2H).

Compound 17: MS: m/z 471.0 (M+H)$^+$; $^1$H NMR (DMSO-d$_6$) δ7.39-7.37 (m, 2H), 7.21 (d, 1H), 7.09 (t, 1H), 6.93-6.86 (m, 1H), 6.79 (d, 1H), 5.72-5.68 (m, 1H), 5.63 (s, 1H), 5.52 (d, 1H), 4.20 (d, 1H), 4.09 (d, 1H), 2.90 (d, 1H), 1.79-1.67 (m, 1H), 1.36-1.31 (m, 1H), 0.90-0.70 (m, 2H).

Compound 18: MS: m/z 486.9 (M+H)$^+$; $^1$H NMR (CDCl$_3$) δ7.26-7.20 (m, 2H), 7.12-6.96 (m, 2H), 6.76 (t, 1H), 6.60 (d, 1H), 5.90 (d, 1H), 5.56 (d, 1H), 5.28 (s, 1H), 4.14 (d, 2H), 2.90 (d, 1H), 2.64 (br, 1H), 1.92-1.87 (m, 1H), 1.73-1.67 (m, 1H), 0.97-0.80 (m, 2H).

Compound 19: MS: m/z 469.0 (M+H)$^+$; $^1$H NMR (CDCl$_3$) δ7.34-7.26 (m, 2H), 7.10-7.09 (m, 2H), 6.99 (d, 1H), 6.84-6.79 (m, 1H), 6.65 (d, 1H), 5.84 (d, 1H), 5.49 (dd, 1H), 5.24 (s, 1H), 4.17 (d, 1H), 4.07 (d, 1H), 2.92 (d, 1H), 1.93-1.88 (m, 1H), 1.75-1.68 (m, 1H), 1.02-0.95 (m, 1H), 0.90-0.83 (m, 1H).

Compound 20: MS: m/z. 467.1 (M+H)$^+$; $^1$H NMR (CDCl$_3$) δ7.28 (d, 1H), 7.09-7.03 (m, 3H), 7.02-6.95 (m, 1H), 6.82-6.77 (m, 1H), 6.62 (d, 1H), 5.85 (d, 1H), 5.53 (dd, 1H), 5.16 (s, 1H), 4.09 (d, 1H), 4.04 (d, 1H), 2.96 (d, 1H), 2.13-2.09 (m, 1H), 2.05-1.96 (m, 1H), 1.06 (d, 3H), 0.69-0.66 (m, 1H).

Compound 21: MS: m/z 467.0 (M+H)$^+$; $^1$H NMR (CDCl$_3$) δ7.30-7.20 (m, 2H), 7.14-6.78 (m, 4H), 6.65 (d, 0.4H), 6.57-6.52 (m, 0.6H), 5.94 (d, 0.6H), 5.85 (d, 0.4H), 5.46-5.33 (m, 1H), 5.22 (s, 0.4H), 5.04 (s, 0.6H), 4.18 (d, 0.6H), 4.06 (d, 0.4H), 3.14-3.02 (m, 1H), 1.87-1.74 (m, 1.4H), 1.66-1.58 (m, 0.6H), 1.35-1.33 (m, 3H), 1.03-0.84 (m, 1.4H), 0.70-0.64 (m, 0.6H).

Compound 22: MS: m/z. 480.1 (M+H)$^+$; $^1$H NMR (CDCl$_3$) δ7.33-7.27 (m, 2H), 7.16-6.96 (m, 3H), 6.91-6.79 (m, 1H), 6.64 (d, 0.5H), 6.57-6.53 (m, 0.5H), 5.94 (d, 0.5H), 5.85 (d, 0.5H), 5.67 (dd, 0.5H), 5.37 (dd, 0.5H), 5.30 (s, 0.5H), 5.13 (s, 0.5H), 4.16 (d, 0.5H), 4.04 (d, 0.5H), 2.82-2.74 (m, 1H), 1.92-1.52 (m, 4H), 1.13-1.02 (m, 4H), 0.97-0.81 (m, 1H).

Compound 23: MS: m/z 503.0 (M+H)$^+$; $^1$H NMR (CDCl$_3$) δ7.36-7.21 (m, 3H), 6.99 (d, 1H), 6.78 (t, 1H), 6.62 (d, 1H), 5.88 (d, 1H), 5.58 (d, 1H), 5.30 (s, 1H), 4.19-4.15 (m, 2H), 2.92 (d, 1H), 2.04-1.06 (m, 3H), 0.96-0.85 (m, 2H).

Compound 24: MS: m/z 487.0 (M+H)$^+$; $^1$H NMR (CDCl$_3$) δ7.36-7.23 (m, 2H), 7.01-6.91 (m, 2H), 6.85-6.81 (m, 1H), 6.51 (d, 1H), 5.89 (d, 1H), 5.54 (d, 1H), 5.31 (s, 1H), 4.18-4.14 (m, 2H), 2.92 (d, 1H), 2.17 (br, 1H), 1.93-1.88 (m, 1H), 1.74-1.69 (m, 1H), 0.97-0.86 (m, 2H).

Compound 25: MS: m/z 479.1 (M+H)$^+$; $^1$H NMR (CDCl$_3$) δ7.33-7.31 (m, 1H), 7.23-6.98 (m, 3H), 6.92-6.85 (m, 1H), 6.81-6.76 (m, 1H), 6.67 (d, 0.5H), 6.60-6.55 (m, 0.5H), 5.92 (d, 0.5H), 5.90-5.78 (m, 1.5H), 5.49 (dd, 0.5H), 5.37 (dd, 0.5H), 5.33-5.27 (m 2H), 5.21 (s, 0.5H), 5.09 (s, 0.5H), 4.18 (d, 0.5H), 4.08 (d, 0.5H), 3.44-3.40 (m, 1H), 1.93-1.87 (m, 1.5H), 1.78-1.74 (m, 0.5H), 1.12-1.07 (m, 0.5H), 0.98-0.90 (m, 1H), 0.72-0.68 (m, 0.5H).

Compound 26: MS: m/z 485.0 (M+H)$^+$; $^1$H NMR (CDCl$_3$) δ7.23 (d, 1H), 7.15-7.07 (m, 2H), 6.70-6.83 (m, 2H), 6.57-6.52 (m, 0.5H), 6.51 (d, 0.5H), 5.96 (d, 0.5H), 5.91 (d, 0.5H), 5.51 (d, 0.5H), 5.46 (d, 0.5H), 5.29 (s, 0.5H), 5.11 (s, 0.5H), 4.24 (d, 0.5H), 4.15 (d, 0.5H), 3.12-3.08 (m, 1H), 1.90-1.76 (m, 1.5H), 1.66-1.64 (m, 0.5H), 1.37-1.33 (m, 3H), 1.05-0.89 (m, 1.5H), 0.72-0.66 (m, 0.5H).

Compound 27: MS: m/z 481.1 (M+H)$^+$; $^1$H NMR (CDCl$_3$) δ7.23 (d, 1H), 7.18-7.16 (m, 1H), 7.10-6.97 (m, 2.5H), 6.91-6.83 (m, 1H), 6.75-6.70 (m, 0.5H), 6.60-6.53 (m, 1H), 5.96 (d, 0.5H), 5.84 (d, 0.5H), 5.48 (dd, 0.5H), 5.35 (dd, 0.5H), 5.25 (s, 0.5H), 5.07 (s, 0.5H), 4.23 (d, 0.5H), 4.16 (d, 0.5H), 3.12-3.03 (m, 1H), 2.34 (s, 1.5H), 2.25 (s, 1.5H), 1.85-1.65 (m, 1.5H), 1.60-1.51 (m, 0.5H), 1.36-1.25 (m, 3H), 1.04-0.89 (m, 1.5H), 0.70-0.67 (m, 0.5H).

Compound 28: MS: m/z. 467.1 (M+H)$^+$; $^1$H NMR (CDCl$_3$) δ7.14-7.02 (m, 4H), 6.83-6.80 (m, 1H), 6.62 (d, 1H), 5.88 (s, 1H), 5.43 (dd, 1H), 5.18 (s, 1H), 4.00 (d, 1H), 3.95 (d, 1H), 2.87 (d, 1H), 2.25 (s, 3H), 1.93-1.87 (m, 1H), 1.64-1.57 (m, 1H), 0.87-0.80 (m, 1H), 0.67-0.60 (m, 1H).

Compound 29: MS: m/z 497.0 (M+H)$^+$; $^1$H NMR (CDCl$_3$) δ7.56-7.54 (m, 2H), 7.40-7.32 (m, 1H), 7.29-7.18 (m, 3H), 6.91-6.83 (m, 2H), 6.05-5.99 (m, 1H), 5.96 (s, 1H), 5.81-5.79 (m, 1H), 4.22-4.19 (m, 1H), 3.60-3.56 (m, 1H), 2.96-2.90 (m, 1H), 2.28 (br, 1H), 2.16-2.10 (m, 1H), 1.51-1.48 (m, 1H), 0.97-0.83 (m, 2H).

Compound 30: MS: m/z. 485.0 (M+H)$^+$; $^1$H NMR (CDCl$_3$) δ7.12-7.02 (m, 2H), 6.98-6.92 (m, 1H), 6.86-6.79 (m, 1H), 6.48 (d, 1H), 5.89 (s, 1H), 5.41 (dd, 1H), 5.30 (s, 1H), 4.09 (d, 1H), 3.98 (d, 1H), 2.87 (d, 1H), 2.25 (s, 3H), 1.94-1.87 (m, 1H), 1.65-1.58 (m, 1H), 0.88-0.81 (m, 1H), 0.66-0.63 (m, 1H).

Compound 31: MS: m/z 481.1 (M+H)$^+$; $^1$H NMR (CDCl$_3$) δ7.09-7.02 (m, 3H), 6.77-6.72 (m, 1H), 6.51 (d, 1H), 5.87 (d, 1H), 5.45 (dd, 1H), 5.20 (s, 1H), 4.08 (d, 1H), 3.96 (d, 1H), 2.87 (d, 1H), 2.21 (s, 3H), 2.19 (s, 3H), 1.93-1.86 (m, 1H), 1.64-1.56 (m, 1H), 0.86-0.79 (m, 1H), 0.64-0.58 (m, 1H).

Compound 32: MS: m/z 525.0 (M+H)$^+$; $^1$H NMR (CDCl$_3$) δ7.31 (d, 1H), 7.12-7.07 (m, 3H), 6.99-6.89 (m, 1H), 6.86-6.76 (m, 1H), 6.63-6.60 (m, 1H), 5.86 (d, 1H), 5.46 (dd, 1H), 5.12 (s, 0.5H), 4.98 (s, 0.5H), 4.13-3.91 (m, 4H), 3.52 (d, 1H), 3.16 (bs, 1H), 2.68 (dd, 1H), 2.17 (dd, 1H), 1.45-1.41 (m, 1H), 1.30-1.21 (m, 3H).

Compound 33: MS: m/z 497.0 (M+H)$^+$; $^1$H NMR (CD$_3$OD) δ7.33 (d, 1H), 7.21-7.12 (m, 2H), 7.06-7.0 (m, 2H), 6.79-6.69 (m, 2H), 5.70 (d, 1H), 5.61-5.57 (m, 1H), 5.39 (s, 0.5H), 5.27 (s, 0.5H), 4.04 (dd, 1H), 3.86 (dd, 1H), 3.43 (d, 1H), 2.74-2.72 (m, 1H), 2.42-2.37 (m, 1H), 1.47-1.45 (m, 1H).

Compound 34: MS: m/z 573.1 (M+H)$^+$; $^1$H NMR (CDCl$_3$) δ7.50-7.31 (m, 4H), 7.22-7.09 (m, 5H), 6.90-6.81 (m, 2H), 6.62-6.60 (m, 1H), 6.19 (d, 1H), 5.48 (d, 1H), 5.04 (s, 1H), 4.41-4.29 (m, 2H), 4.11-4.07 (m, 2H), 3.63-3.47 (m, 1H), 3.23-3.07 (m, 1H), 2.96 (d, 1H), 2.58 (bs, 1H), 2.19-1.97 (m, 1H), 1.72-1.71 (m, 1H), 0.87-0.85 (m, 1H).

Compound 35: MS: m/z 485.0 (M+H)$^+$; $^1$H NMR (CDCl$_3$) δ7.23 (d, 1H), 7.11-7.05 (m, 1H), 7.00-6.89 (m, 2H), 6.83-6.76 (m, 1H), 6.47 (d, 1H), 5.88 (d, 1H), 5.56 (dd, 1H), 5.22 (s, 1H), 4.15 (d, 1H), 4.06 (d, 1H), 2.95 (d, 1H), 2.13-2.11 (m, 1H), 2.10-2.09 (m, 1H), 1.06 (d, 3H), 0.68-0.64 (m, 1H).

Compound 36: MS: m/z 481.1 (M+H)$^+$; $^1$H NMR (CDCl$_3$) δ7.23 (d, 1H), 7.08-6.95 (m, 3H), 6.74-6.69 (m, 1H), 6.50 (d, 1H), 5.83 (d, 1H), 5.57 (dd, 1H), 5.18 (s, 1H), 4.15 (d, 1H), 4.05 (d, 1H), 2.96 (d, 1H), 2.25 (s, 3H), 2.12-2.08 (m, 1H), 2.04-1.94 (m, 1H), 1.05 (d, 3H), 0.68-0.65 (m, 1H).

Compound 37: MS: m/z 481.1 (M+H)$^+$; $^1$H NMR (CDCl$_3$) δ7.29 (d, 1H), 7.11-7.03 (m, 3H), 7.01-6.96 (m, 1H), 6.82-6.78 (m, 1H), 6.62 (d, 1H), 5.84 (d, 1H), 5.52 (dd, 1H), 5.17 (s, 1H), 4.08 (d, 2H), 4.04 (d, 1H), 2.98 (d, 1H), 2.08-2.05 (m, 1H), 1.94-1.89 (m, 1H), 1.43-1.36 (m, 1H), 1.16-1.07 (m, 1H), 1.02-1.97 (m, 3H), 0.67-0.68 (m, 1H).

Compound 38: MS: m/z 497.1 (M+H)$^+$; $^1$H NMR (CDCl$_3$) δ7.28 (d, 1H), 7.11-7.03 (m, 3H), 6.99-6.95 (m, 1H), 6.82-6.76 (m, 1H), 6.62 (d, 1H), 5.84 (d, 1H), 5.52 (dd, 1H), 5.15 (s, 1H), 4.20 (d, 1H), 4.07 (d, 1H), 3.64-3.58 (m, 1H), 3.25 (s, 3H), 3.05 (d, 1H), 3.04-2.80 (m, 1H), 2.20-2.17 (m, 1H), 2.07-2.01 (m, 1H), 0.91-0.82 (m, 1H).

Compound 39: MS: m/z 457.1 (M+H)$^+$; $^1$H NMR (CDCl$_3$) δ 7.27 (d, 1H), 7.11-6.97 (m, 2H), 5.84 (d, 1H), 5.50 (dd, 1H), 5.23 (d, 1H), 4.16 (d, 1H), 4.05 (d, 1H), 2.92 (d, 1H), 1.93-1.84 (m, 1H), 1.74-1.68 (m, 1H), 1.01-0.94 (m, 1H), 0.90-0.83 (m, 1H).

Synthesis and Characterization of Compound 40

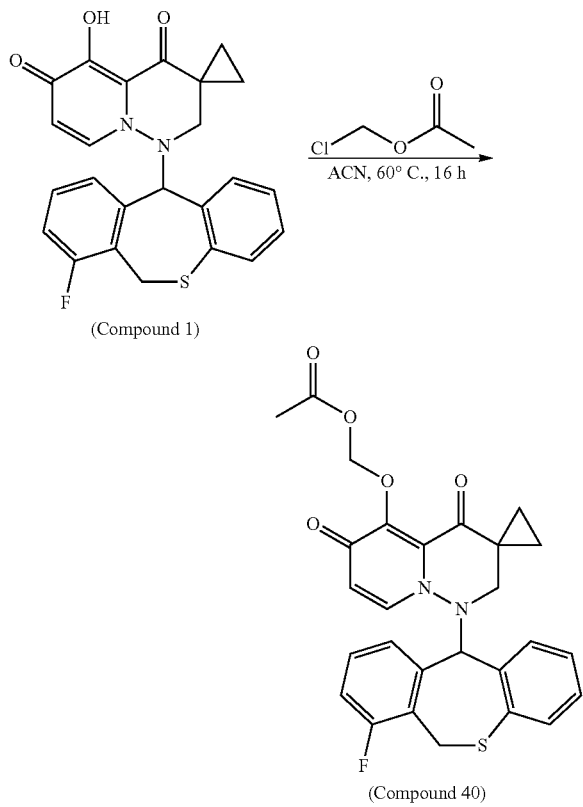

Compound 1 (0.033 g, 0.076 mmole) was dissolved in CH$_3$CN (6 ml), and K$_2$CO$_3$ (0.315 g, 2.28 mmole), NaI catalyst and chloromethyl acetate (0.050 g, 0.46 mmole) were added. Then the mixture was stirred at 60° C. for 16 hours. The mixture solution was concentrated under reduced pressure and purified by PLC to afford Compound 40 (6.1 mg, yield: 16%) MS: m/z 507.1 (M+H)$^+$; $^1$H NMR (CDCl$_3$) δ7.32-7.04 (m, 6H), 6.89-6.84 (m, 1H), 6.76 (d, 1H), 5.98 (d, 1H), 5.92 (d, 1H), 5.80 (d, 1H), 5.44 (dd, 1H), 5.18 (s, 1H), 4.12 (d, 1H), 4.06 (d, 1H), 2.91 (d, 1H), 2.14 (s, 3H), 1.94-1.90 (m, 1H), 1.50-1.44 (m, 1H), 0.88-0.77 (m, 2H).

Synthesis and Characterization of Compounds 41-61

Each of compounds 41-61 was prepared following the similar protocols described in the preparation of compound 40.

Analytical data of compounds 41-61 are listed below.

Compound 41: MS: m/z. 552.1 (M+H)$^+$; $^1$H NMR (CDCl$_3$) δ7.23 (d, 1H), 7.08-7.01 (m, 3H), 6.98-6.90 (m, 1H), 6.72 (d, 1H), 5.97 (d, 1H), 5.48 (dd, 1H), 5.16 (s, 1H), 4.20 (d, 1H), 4.04 (d, 1H), 3.60-3.33 (m, 4H), 2.90 (d, 1H), 1.93-1.87 (m, 1H), 1.57-1.41 (m, 1H), 1.38-1.28 (m, 6H), 0.87-0.74 (m, 2H).

Compound 42: MS: m/z 716.1 (M+H)$^+$; $^1$H NMR (CDCl$_3$) δ7.36-7.26 (m, 4H), 7.20-6.97 (m, 6H), 6.88-6.27 (m, 2H), 6.28 (d, 0.5H), 6.15 (d, 0.5H), 6.00-5.95 (m, 1H), 5.87 (d, 0.5H), 5.74 (d, 0.5H), 5.48-5.43 (m, 1.5H), 5.24-5.10 (m, 2.5H), 5.01 (d, 0.5H), 4.75 (d, 0.5H), 4.54-4.49 (m, 0.5H), 4.36-4.31 (m, 0.5H), 4.11-4.00 (m, 2H), 2.88-2.82 (m, 1H), 2.50-2.47 (m, 0.5H), 2.24-2.17 (m, 0.5H), 2.00-1.98 (m, 0.5H), 1.90-1.85 (m, 0.5H), 1.46-1.39 (m, 1H), 1.05-0.68 (m, 8H).

Compound 43: MS: m/z 579.1 (M+H)$^+$; $^1$H NMR (CDCl$_3$) δ7.28 (d, 1H), 7.09-7.05 (m, 3H), 7.02-6.95 (m, 1H), 6.91-6.89 (m, 1H), 6.81-6.74 (m, 1H), 5.99 (d, 01H), 5.48 (dd, 1H), 5.16 (s, 1H), 4.16 (d, 1H), 4.04 (d, 1H), 2.91 (d, 1H), 2.71-2.66 (m, 2H), 1.92-1.88 (m, 1H), 1.83-1.71 (m, 2H), 1.70-1.59 (m, 2H), 1.65-1.50 (m, 1H), 1.47-1.34 (m, 6H), 0.97-0.77 (m, 5H).

Compound 44: MS: m/z 543.1 (M+H)$^+$; $^1$H NMR (CDCl$_3$) δ7.50-7.47 (m, 2H), 7.36-7.21 (m, 4H), 7.07-6.95 (m, 4H), 6.76-6.71 (m, 1H), 6.53 (d, 1H), 5.96 (d, 1H), 5.49-5.40 (m, 3H), 5.09 (s, 1H), 4.04-3.95 (m, 2H), 2.83 (d, 1H), 1.94-1.89 (m, 1H), 1.39-1.34 (m, 1H), 0.76-0.65 (m, 2H).

Compound 45: MS: m/z 541.0 (M$^+$+1); $^1$H NMR (CDCl$_3$) δ7.31 (d, 1H), 7.06-7.00 (m, 4H), 6.85-6.84 (m, 1H), 6.73 (d, 1H), 6.03 (d, 1H), 5.96 (d, 1H), 5.80 (d, 1H), 5.49 (d, 1H), 5.15 (s, 1H), 4.13 (d, 1H), 4.05 (d, 1H), 3.87 (s, 3H), 2.91 (d, 1H), 1.95-1.90 (m, 1H), 1.49-1.48 (m, 1H), 0.88-0.76 (m, 2H).

Compound 46: MS: m/z 555.1 (M+H)$^+$; $^1$H NMR (CDCl$_3$) δ7.23 (d, 0.5H), 7.18 (d, 0.5H), 7.14-7.09 (m, 2H), 7.05-6.92 (m, 2H), 6.87-6.84 (m, 0.5H), 6.72-6.70 (m, 0.5H), 6.57-6.55 (m, 0.5H), 6.44-6.42 (m, 0.5H), 5.97 (d, 0.5H), 5.94 (d, 0.5H), 5.53-5.44 (m, 1H), 5.14 (s, 0.5H), 5.12 (s, 0.5H), 4.14-4.09 (m, 1H), 4.06 (d, 0.5H), 4.01 (d, 0.5H), 3.83 (s, 1.5H), 3.68 (s, 1.5H), 3.03-2.872 (m, 1H), 1.97-1.91 (m, 1H), 1.80-1.78 (m, 3H), 1.47-1.32 (m, 1H), 0.85-0.71 (m, 2H).

Compound 47: MS: m/z 539.1 (M+H)$^+$; $^1$H NMR (CDCl$_3$) δ7.22 (d, 1H), 7.10-7.01 (m, 3H), 6.79 (t, 1H), 6.62 (d, 1H), 5.96 (d, 1H), 5.91 (d, 1H), 5.80 (d, 1H), 5.53 (dd, 1H), 5.17 (s, 1H), 4.13 (d, 1H), 4.12 (d, 1H), 2.90 (d, 1H), 2.25 (s, 3H), 2.14 (s, 3H), 1.94-1.89 (m, 1H), 1.50-1.43 (m, 1H), 0.85-0.73 (m, 2H).

Compound 48: MS: m/z 538.1 (M+H)$^+$; $^1$H NMR (CDCl$_3$) δ7.21-7.29 (m, 1H), 7.09-6.90 (m, 3H), 6.80-6.59 (m, 2H), 5.97 (d, 1H), 5.51 (d, 1H), 5.20 (bs, 1H), 4.19-4.10 (m, 2H), 3.16-2.98 (m, 6H), 2.90 (d, 1H), 2.25 (s, 3H), 1.91-1.87 (m, 1H), 1.52 (m, 1H), 0.83-0.73 (m, 2H).

Compound 49: MS: m/z 579.1 (M+H)$^+$; $^1$H NMR (CDCl$_3$) δ7.29-7.26 (m, 1H), 7.07-7.01 (m, 3H), 6.80-6.75 (m, 1H), 6.56 (d, 1H), 5.95 (d, 1H), 5.52-5.47 (m, 1H), 5.29 (d, 1H), 5.20-5.16 (m, 2H), 4.17-4.07 (m, 2H), 2.95-2.88 (m, 1H), 2.25 (s, 3H), 2.14 (s, 3H), 1.98-1.93 (m, 1H), 1.54-1.47 (m, 1H), 0.87-0.74 (m, 2H).

Compound 50: MS: m/z 555.1 (M+H)$^+$; $^1$H NMR (CDCl$_3$) δ7.28 (d, 1H), 7.10-6.97 (m, 3H), 6.77 (t, 1H), 6.60 (d, 1H), 6.06 (d, 1H), 5.96 (d, 1H), 5.78 (d, 1H), 5.55-5.50 (m, 1H), 5.18 (s, 1H), 4.16-4.12 (m, 2H), 3.87 (s, 3H), 2.92 (d, 1H), 2.25 (s, 3H), 1.95-1.90 (m, 1H), 1.52-1.46 (m, 1H), 0.88-0.73 (m, 2H).

Compound 51: MS: m/z 583.1 (M+H)$^+$; $^1$H NMR (CDCl$_3$) δ7.28 (d, 1H), 7.10-6.91 (m, 3H), 6.78 (t, 1H), 6.69 (d, 1H), 6.11 (d, 1H), 5.96 (d, 1H), 5.79 (d, 1H), 5.52 (d, 1H), 5.17 (s, 1H), 5.02-4.94 (m, 1H), 4.16-4.12 (m, 2H) 2.92 (d, 1H), 2.25 (s, 3H), 1.91-1.88 (m, 1H), 1.44-1.26 (m, 7H), 0.90-0.75 (m, 2H).

Compound 52: MS: m/z 542.8 (M+H)$^+$; $^1$H NMR (CDCl$_3$) δ7.23 (d, 1H), 7.13-6.85 (m, 4H), 6.61 (d, 1H), 6.00 (d, 1H), 5.93 (d, 1H), 5.77 (d, 1H), 5.53 (dd, 1H), 5.21 (s, 1H), 4.15-4.10 (m, 2H), 2.90 (d, 1H), 2.14 (s, 3H), 1.95-1.89 (m, 1H), 1.51-1.44 (m, 1H), 0.87-0.71 (m, 2H).

Compound 53: MS: m/z 583.0 (M+H)$^+$; $^1$H NMR (CDCl$_3$) δ7.28 (d, 1H), 7.13-6.83 (m, 4H), 6.55 (d, 1H), 6.01 (d, 1H), 5.50 (dd, 1H), 5.33-5.15 (m, 3H), 4.16-4.12 (m, 2H), 2.91 (d, 1H), 2.11 (s, 3H), 1.98-1.93 (m, 1H), 1.54-1.47 (m, 1H), 0.82-0.71 (m, 2H).

Compound 54: MS: m/z 559.0 (M+H)+; 1H NMR (CDCl3) δ7.30 (d, 1H), 7.14-6.83 (m, 4H), 6.59 (d, 1H), 6.15 (d, 1H), 5.97 (d, 1H), 5.80 (d, 1H), 5.53 (dd, 1H), 5.22 (s, 1H), 4.16-4.12 (m, 2H), 3.87 (s, 3H), 2.92 (d, 1H), 1.96-1.92 (m, 1H), 1.54-1.47 (m, 1H), 0.88-0.73 (m, 2H).

Compound 55: MS: m/z 493.1 (M+H)+; 1H NMR (CDCl3) δ7.32-7.24 (m, 3H), 7.16 (d, 1H), 7.09-7.07 (m, 2H), 6.87-6.78 (m, 2H), 6.01 (d, 1H), 5.72 (d, 1H), 5.15 (s, 1H), 4.15 (d, 1H), 3.50 (d, 1H), 2.91 (d, 1H), 2.41 (s, 3H), 1.92-1.89 (m, 1H), 1.55-1.52 (m, 1H), 0.90-0.83 (m, 2H).

Compound 56: MS: m/z 525.0 (M+H)+; 1H NMR (CDCl3) δ7.24-7.22 (m, 2H), 7.23 (d, 1H), 7.06 (dd, 1H), 7.01-6.86 (m, 3H), 6.61 (d, 1H), 6.00 (d, 1H), 5.93 (d, 1H), 5.80 (d, 1H), 5.76 (d, 1H), 5.19 (s, 1H), 4.09 (d, 1H), 3.58 (d, 1H), 2.88 (d, 1H), 2.14 (s, 3H), 1.96-1.84 (m, 1H), 1.49-1.44 (m, 1H), 0.82-0.74 (m, 2H).

Compound 57: MS: m/z 561.1 (M+H)+; 1H NMR (CDCl3) δ7.29-7.20 (m, 2H), 7.04-6.93 (m, 3H), 6.76 (t, 1H), 6.56 (d, 1H), 5.95 (d, 1H), 5.76 (d, 1H), 5.31-5.16 (m, 3H), 4.07 (d, 1H), 3.60 (d, 1H), 2.90 (d, 1H), 2.45 (s, 3H), 2.15 (s, 3H), 1.98-1.93 (m, 1H), 1.53-1.46 (m, 1H), 0.90-0.71 (m, 2H).

Compound 58: MS: m/z 539.1 (M+H)+; 1H NMR (CDCl3) δ7.31-7.22 (m, 3H), 7.15-6.88 (m, 3H), 6.77-6.67 (m, 1H), 6.06 (d, 0.75H), 6.00 (d, 0.25H), 5.87-5.80 (m, 2H), 5.43 (d, 0.25H), 5.28 (d, 0.75H), 5.15 (s, 0.25H), 5.00 (s, 0.75H), 4.14 (d, 0.75H), 4.05 (d, 0.25H), 3.12-3.06 (m, 1H), 2.12 (s, 3H), 1.96-1.89 (m, 1H), 1.59-1.45 (m, 1H), 1.37-1.25 (m, 3H), 0.94-0.83 (m, 1H), 0.63-0.48 (m, 1H).

Compound 59: MS: m/z 539.1 (M+H)+; 1H NMR (CDCl3) δ7.26 (d, 1H), 7.09-7.05 (m, 3H), 7.02-6.97 (m, 1H), 6.90-6.95 (m, 1H), 6.72 (d, 1H), 5.94 (d, 1H), 5.87 (d, 1H), 5.79 (d, 1H), 5.52 (dd, 1H), 5.07 (s, 1H), 4.14 (d, 1H), 4.05 (d, 1H), 4.02 (d, 1H), 2.92 (d, 1H), 2.14 (s, 3H), 2.12-2.10 (m, 1H), 1.76-1.70 (m, 1H), 1.03 (d, 3H), 0.47-0.44 (m, 1H).

Compound 60: MS: m/z. 557.1 (M+H)+; 1H NMR (CDCl3) δ7.22 (d, 1H), 7.17-6.97 (m, 2H), 6.93-6.85 (m, 2H), 6.59 (d, 1H), 6.01 (d, 1H), 5.92 (d, 1H), 5.68 (d, 1H), 5.55 (dd, 1H), 5.14 (s, 1H), 4.14 (dd, 1H), 4.02 (d, 1H), 2.92 (d, 1H), 2.15 (s, 3H), 2.14-2.10 (m, 1H), 1.75-1.68 (m, 1H), 1.03 (d, 3H), 0.45-0.43 (m, 1H).

Compound 61: MS: m/z 553.1 (M+H)+; 1H NMR (CDCl3) δ7.23 (d, 1H), 7.17-6.97 (m, 3H), 6.82-6.77 (m, 1H), 6.59 (d, 1H), 5.96 (d, 1H), 5.90 (d, 1H), 5.79 (d, 1H), 5.70 (dd, 1H), 5.10 (s, 1H), 4.14 (d, 1H), 4.02 (d, 1H), 2.93 (d, 1H), 2.25 (s, 3H), 2.14 (s, 3H), 2.13-2.10 (m, 1H), 1.75-1.67 (m, 1H), 1.03 (d, 3H), 0.45-0.43 (m, 1H).

Shown in the table below are the structures of compounds 40-61.

Compound 40

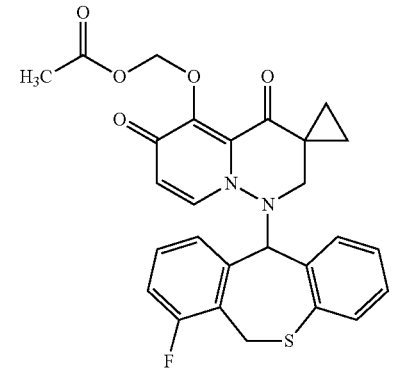 [SMILES: CC(=O)OCOc1c2n(ccc1=O)N(C1c3ccccc3SCc3c(F)cccc31)CC1(CC1)C2=O]

Compound 41

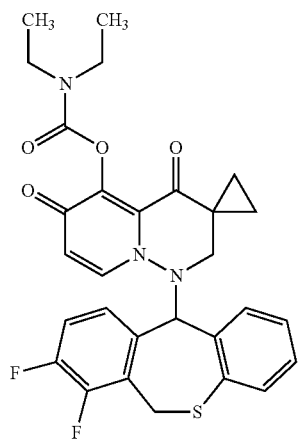 [SMILES: CCN(CC)C(=O)Oc1c2n(ccc1=O)N(C1c3ccccc3SCc3c1ccc(F)c3F)CC1(CC1)C2=O]

Compound 42

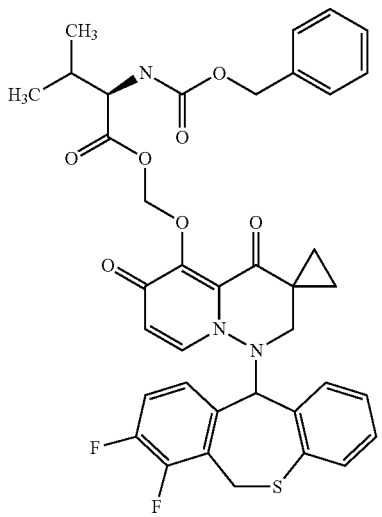 [SMILES: CC(C)[C@@H](NC(=O)OCc1ccccc1)C(=O)OCOc1c2n(ccc1=O)N(C1c3ccccc3SCc3c1ccc(F)c3F)CC1(CC1)C2=O]

Compound 43

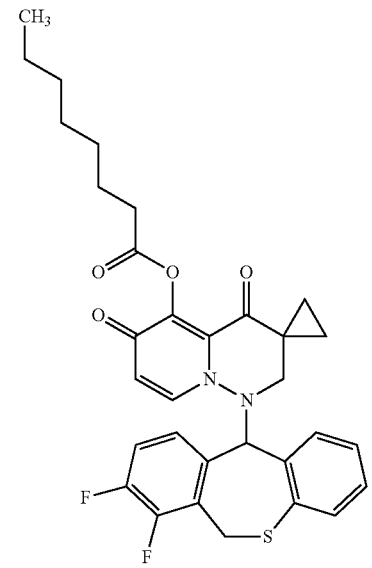 [SMILES: CCCCCCCC(=O)Oc1c2n(ccc1=O)N(C1c3ccccc3SCc3c1ccc(F)c3F)CC1(CC1)C2=O]

-continued
Compound 44
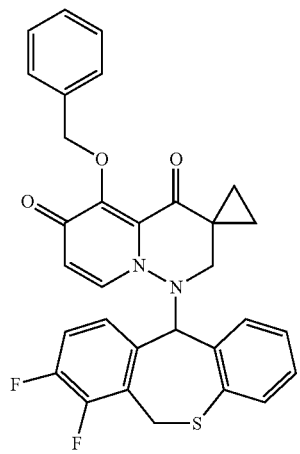 [SMILES: O=C1c2c(OCc3ccccc3)c(=O)ccn2N(C2c3ccccc3SCc3c2ccc(F)c3F)CC12CC2]
Compound 45
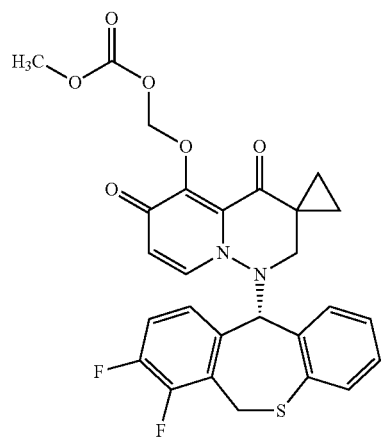 [SMILES: COC(=O)OCOc1c2n(ccc1=O)N([C@@H]1c3ccccc3SCc3c1ccc(F)c3F)CC1(CC1)C2=O]
Compound 46
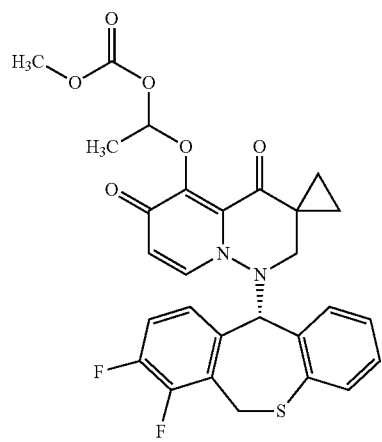 [SMILES: COC(=O)OC(C)Oc1c2n(ccc1=O)N([C@@H]1c3ccccc3SCc3c1ccc(F)c3F)CC1(CC1)C2=O]
-continued
Compound 47
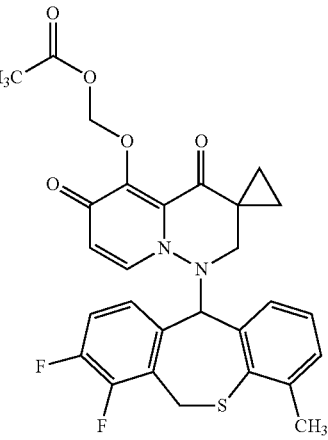
Compound 48
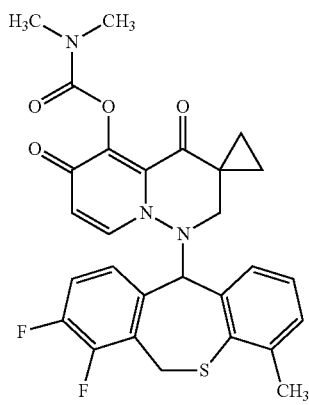 [SMILES: Cc1cccc2c1SCc1c(ccc(F)c1F)C2N1CC2(CC2)C(=O)c2c(OC(=O)N(C)C)c(=O)ccn21]
Compound 49
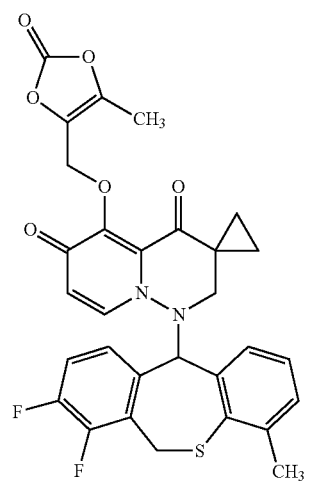 [SMILES: Cc1cccc2c1SCc1c(ccc(F)c1F)C2N1CC2(CC2)C(=O)c2c(OCc3oc(=O)oc3C)c(=O)ccn21]

-continued
Compound 50
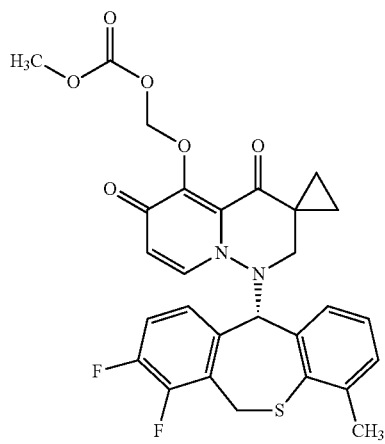 [SMILES: COC(=O)OCOc1c2n(ccc1=O)N([C@H]1c3ccc(F)c(F)c3CSc3c(C)cccc31)CC1(CC1)C2=O]
Compound 51
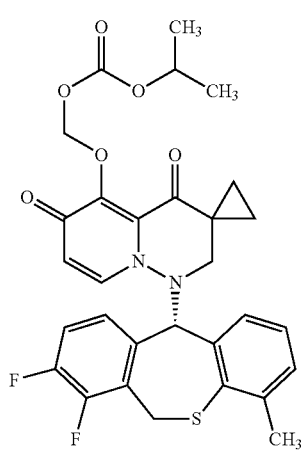
Compound 52
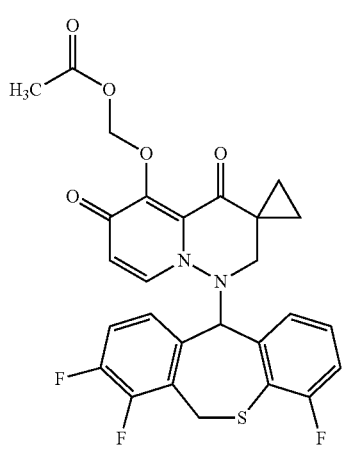 [SMILES: CC(=O)OCOc1c2n(ccc1=O)N(C1c3ccc(F)c(F)c3CSc3c(F)cccc31)CC1(CC1)C2=O]
-continued
Compound 53
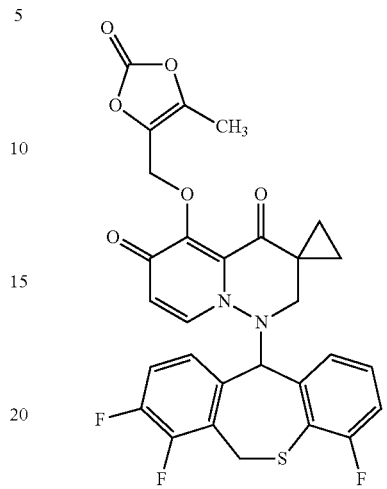
Compound 54
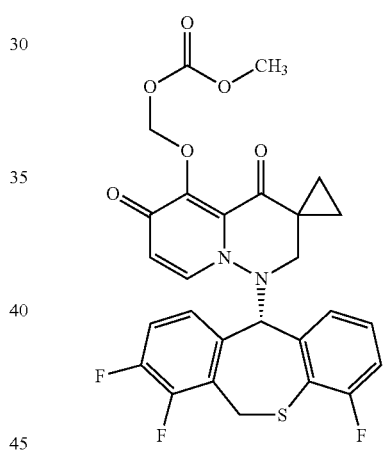
Compound 55
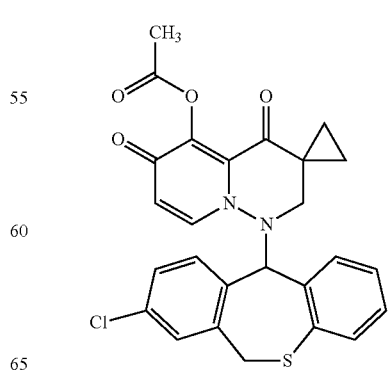

Compound 56

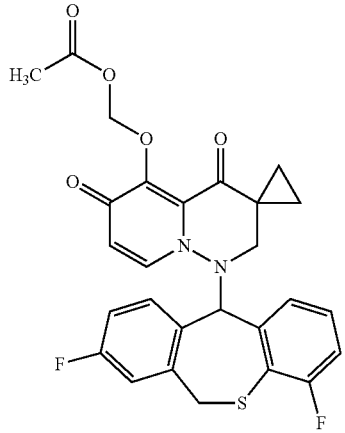 [SMILES: CC(=O)OCOc1c2n(ccc1=O)N(C1c3ccc(F)cc3CSc3c(F)cccc31)CC1(CC1)C2=O]

Compound 57

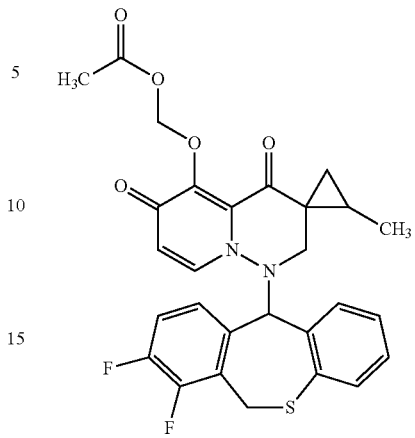

Compound 58

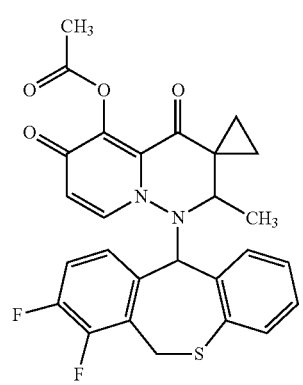 [SMILES: CC(=O)Oc1c2n(ccc1=O)N(C1c3ccccc3SCc3c1ccc(F)c3F)C(C)C1(CC1)C2=O]

Compound 59

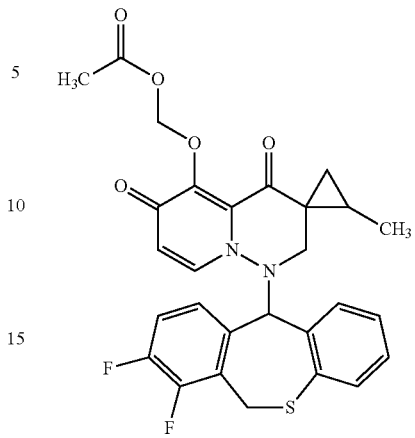

Compound 60

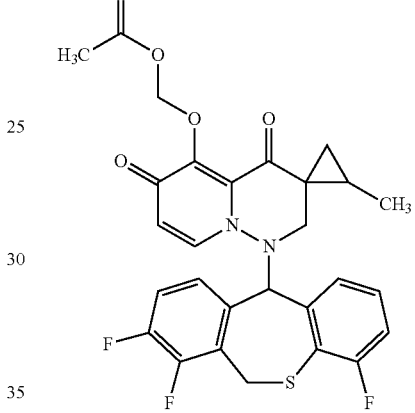

Compound 61

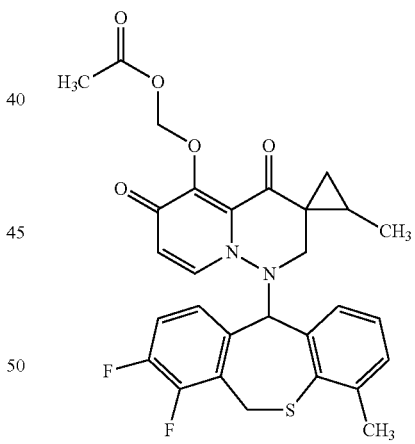

EXAMPLE 2

Cytopathic Effect (CPE) Reduction Assay

A CPE reduction assay was performed as follows to evaluate the potency of test compounds in inhibiting the activity of influenza viruses.

Confluent MDCK cells in 96-well tissue culture plates were incubated with test compounds and influenza A or B viruses at low multiplicity of infection for 72 h at 37° C. The plates were fixed by adding 0.5% formaldehyde, followed by staining with 0.5% Crystal Violet. Subsequently, the plates were measured at 570 nm with a microplate reader (Multiskan Ascent, Thermo). The concentration required for a test compound to reduce the virus-induced CPE by 50% relative to the virus control was expressed as the 50% effective dose ($EC_{50}$).

Compounds 1-39 were tested using the CPE reduction assay. For influenza A virus infection, it was observed that 30 test compounds (i.e., Compounds 1-10, 13, 16-22, 25, 27-30, 32-33, 35-38 and 39) unexpectedly exhibited $EC_{50}$ values lower than 0.1 μM and 9 test compounds (i.e., Compounds 11-12, 14-15, 23-24, 26, 31, and 34) exhibited $EC_{50}$ values of 0.1-1 μM. On the other hand, for influenza B virus infection, it was observed that 15 test compounds (i.e., Compounds 2-5, 7-9, 14-15, 17, 24, 35, 37-38 and 39) unexpectedly exhibited $EC_{50}$ values lower than 0.1 μM and 24 test compounds (i.e., Compounds 1, 6, 10-13, 16, 18-23, 25-34, and 36) exhibited $EC_{50}$ values of 0.1-1 μM.

Further, it was observed that compounds of this disclosure containing the cyclopropyl moiety in Formula (I) unexpectedly exhibited higher potency in inhibiting the activity of influenza viruses than structurally close analogs not containing the cyclopropyl moiety. The results of the difference in anti-influenza virus activity between the comparative compounds (structurally close analogs not containing the cyclopropyl moiety) and the example compounds (containing the cyclopropyl moiety) are shown in the following table.

| Comparative compound | $A_1$ | $A_2$ | $A_3$ | $Y_1$ | $X_1$ | $X_2$ | $X_3$ | $X_4$ | R | Compare with | Activity difference (folds)* Influenza A virus | Influenza B virus |
|---|---|---|---|---|---|---|---|---|---|---|---|---|
| A1 | CH | N | $CH_2$ | S | H | F | H | H |  | Compound 1 | 2.2 | — |
| A2 | CH | N | $CH_2$ | S | H | F | H | H |  | Compound 1 | 6.6 | 2.2 |
| A3 | CH | N | $CH_2$ | S | H | F | H | H |  | Compound 1 | 5.0 | — |
| A4 | CH | N | $CH_2$ | S | H | F | H | H |  | Compound 1 | 15.3 | 2.5 |
| A5 | CH | N | $CH_2$ | S | H | F | H | H |  | Compound 1 | 4.6 | 2.9 |
| B1 | CH | N | $CH_2$ | S | F | F | H | H |  | Compound 2 | 7.2 | 3.0 |
| B2 | CH | N | $CH_2$ | S | F | F | H | H |  | Compound 2 | 3.9 | 3.3 |
| B3 | CH | N | $CH_2$ | S | F | F | H | H | | Compound 2 | 57.9 | — |
| B4 | CH | N | $CH_2$ | S | F | F | H | H |  | Compound 2 | 8.0 | 4.4 |

-continued

| Comparative compound | $A_1$ | $A_2$ | $A_3$ | $Y_1$ | $X_1$ | $X_2$ | $X_3$ | $X_4$ | R | Compare with | Activity difference (folds)* Influenza A virus | Influenza B virus |
|---|---|---|---|---|---|---|---|---|---|---|---|---|
| C1 | CH | N | $CH_2$ | S | F | H | Cl | H |  | Compound 3 | 2.0 | — |
| C2 | CH | N | $CH_2$ | S | F | H | Cl | H |  | Compound 3 | 4.8 | — |
| C3 | CH | N | $CH_2$ | S | F | H | Cl | H |  | Compound 3 | 9.4 | 3.0 |
| C4 | CH | N | $CH_2$ | S | F | H | Cl | H |  | Compound 3 | 37.1 | 8.0 |
| C5 | CH | N | $CH_2$ | S | F | H | Cl | H |  | Compound 3 | 17.9 | 2.7 |
| D1 | CH | N | $CH_2$ | S | Cl | H | H | H |  | Compound 4 | 5.4 | — |
| D2 | CH | N | $CH_2$ | S | Cl | H | H | H |  | Compound 4 | 3.8 | — |
| D3 | CH | N | $CH_2$ | S | Cl | H | H | H |  | Compound 4 | 5.6 | 2.5 |
| D4 | CH | N | $CH_2$ | S | Cl | H | H | H |  | Compound 4 | 10.1 | 5.8 |
| D5 | CH | N | $CH_2$ | S | Cl | H | H | H |  | Compound 4 | 10.3 | 8.4 |
| E1 | CH | N | $CH_2$ | S | Cl | H | $CH_3$ | H |  | Compound 6 | 2.4 | — |
| E2 | CH | N | $CH_2$ | S | Cl | H | $CH_3$ | H |  | Compound 6 | 9.2 | 1.9 |
| E3 | CH | N | $CH_2$ | S | Cl | H | $CH_3$ | H |  | Compound 6 | 3.8 | — |

-continued

| Comparative compound | A₁ | A₂ | A₃ | Y₁ | X₁ | X₂ | X₃ | X₄ | R | Compare with | Activity difference (folds)* Influenza A virus | Influenza B virus |
|---|---|---|---|---|---|---|---|---|---|---|---|---|
| F1 | CH | N | CH₂ | S | F | H | CH₃ | H |  | Compound 7 | 4.6 | 2.6 |
| F2 | CH | N | CH₂ | S | F | H | CH₃ | H |  | Compound 7 | 4.1 | 2.1 |
| F3 | CH | N | CH₂ | S | F | H | CH₃ | H |  | Compound 7 | 16.0 | 3.8 |
| F4 | CH | N | CH₂ | S | F | H | CH₃ | H |  | Compound 7 | 30.0 | 10.8 |
| F5 | CH | N | CH₂ | S | F | H | CH₃ | H |  | Compound 7 | 27.1 | 5.5 |
| G1 | CH | N | CH₂ | S | F | H | H | H |  | Compound 8 | 6.8 | 2.6 |
| G2 | CH | N | CH₂ | S | F | H | H | H |  | Compound 8 | 5.0 | 2.4 |
| G3 | CH | N | CH₂ | S | F | H | H | H |  | Compound 8 | 5.0 | 3.3 |
| H1 | CH | N | CH₂ | S | H | H | F | H |  | Compound 9 | 4.7 | 2.9 |
| H2 | CH | N | CH₂ | S | H | H | F | H |  | Compound 9 | 8.9 | 2.9 |
| H3 | CH | N | CH₂ | S | H | H | F | H |  | Compound 9 | 27.7 | 10.4 |
| H4 | CH | N | CH₂ | S | H | H | F | H |  | Compound 9 | 5.4 | 3.1 |
| I1 | CH | N | CH₂ | S | H | H | CH₃ | H |  | Compound 11 | 3.1 | — |

-continued

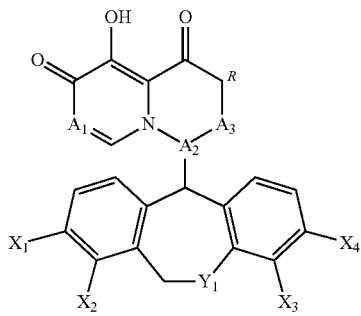

|Comparative compound|$A_1$|$A_2$|$A_3$|$Y_1$|$X_1$|$X_2$|$X_3$|$X_4$|R|Compare with|Influenza A virus|Influenza B virus|
|---|---|---|---|---|---|---|---|---|---|---|---|---|
|J1|CH|N|$CH_2$|S|Cl|H|F|H||Compound 14|4.5|—|
|J2|CH|N|$CH_2$|S|Cl|H|F|H||Compound 14|3.2|—|
|J3|CH|N|$CH_2$|S|Cl|H|F|H||Compound 14|4.9|5.1|
|K1|CH|N|$CH_2$|O|F|H|Cl|H||Compound 15|3.2|2.9|
|K2|CH|N|$CH_2$|O|F|H|Cl|H||Compound 15|8.0|2.1|
|L1|CH|N|$CH_2$|S|F|F|$CH_3$|H||Compound 16|15.4|3.5|
|L2|CH|N|$CH_2$|S|F|F|$CH_3$|H||Compound 16|16.7|27.9|
|M1|CH|N|$CH_2$|S|F|F|F|H||Compound 17|94.4|13.6|
|M2|CH|N|$CH_2$|S|F|F|F|H||Compound 17|4.9|—|
|N1|CH|N|$CH_2$|S|Cl|F|H|H||Compound 19|3.1|—|
|N2|CH|N|$CH_2$|S|Cl|F|H|H||Compound 19|3.6|—|
|O1|CH|N|$CH_2$|S|Cl|F|F|H||Compound 24|3.9|—|

*Activity difference = ($EC_{50}$ value of a comparative compound)/($EC_{50}$ value of an example compound)

These results indicate that the compounds of this disclosure unexpectedly exhibited higher potency in inhibiting the activity of influenza viruses, as compared to their structurally close analogs.

EXAMPLE 3

Survival Rate of Influenza Virus 24 Hours Post-Infection

Tests were performed as follows to evaluate the effect of compounds of Formula (I) on the survival rates of mice 24 hours post-infection in an influenza A mouse model.

Mice were first infected with 100 or 500 pfu/mouse influenza A virus, followed by dosing of compounds of formula (I) 24 hours post-infection. The dosing was administered twice daily for 5 days. Each compound was orally administered to mice at a dosage of 5, 10, or 20 mg/kg. Mice infected with 100 or 500 pfu/mouse demonstrated extremely high mortality. Unexpectedly, it was observed that mice treated with compounds of Formula (I), e.g., Compound 1 and Compound 2, exhibited survival rates of 80-100%, as compared to a survival rate of 16.7% exhibited by mice treated with oseltamivir and a survival rate of 14.3% exhibited by mice treated with comparative compound B1. Note that oseltamivir is a commercial drug for treating influenza, and comparative compound B1 is a structurally close analog of Compound 2.

These results indicate that compounds of Formula (I) unexpectedly exhibited high efficacy in treating influenza.

OTHER EMBODIMENTS

All of the features disclosed in this specification may be combined in any combination. Each feature disclosed in this specification may be replaced by an alternative feature serving the same, equivalent or similar purpose. Thus, unless expressly stated otherwise, each feature disclosed is only an example of a series of equivalent or similar features.

From the above description, one skilled in the art can easily ascertain the characteristics of the present disclosure, and without departing from the spirit and scope thereof, can make various changes and modifications of the disclosure to adapt it to various usage and conditions. Thus, other embodiments are also within the scope of the following claims.

What is claimed is:

1. A compound of Formula (I) below, or a pharmaceutically acceptable salt thereof, (I)

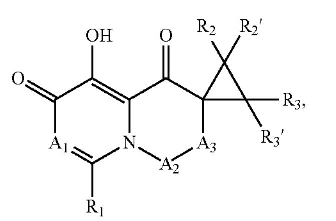

wherein:

$R_1$ is hydrogen, deuterium, halogen, cyano, hydroxyl, carboxyl, amino, $C_{1-6}$ alkyl, $C_{2-6}$ alkenyl, $C_{2-6}$ alkynyl, $C_{1-6}$ alkoxy, $C_{1-6}$ alkylamine, $C_{3-20}$ carbocyclyl, or $C_{3-20}$ heterocyclyl;

each of $R_2$, $R_2'$, $R_3$, and $R_3'$, independently, is hydrogen, deuterium, halogen, cyano, hydroxyl, carboxyl, amino, formyl, nitro, $C_{1-6}$ alkyl, $C_{2-6}$ alkenyl, $C_{2-6}$ alkynyl, $C_{1-6}$ alkoxy, $C_{2-6}$ alkenyloxy, $C_{1-6}$ alkylcarbonyl, $C_{1-6}$ alkyloxycarbonyl, $C_{1-6}$ alkylamine, $C_{3-20}$ carbocyclyl, or $C_{3-20}$ heterocyclyl;

$A_1$ is $CR_4$ or N;

$A_2$ is $CR_5R_6$ or $NR_7$;

$A_3$ is $CR_5'R_6'$ or $NR_7'$;

$R_4$ is hydrogen, deuterium, halogen, cyano, hydroxyl, carboxyl, amino, $C_{1-6}$ alkyl, $C_{2-6}$ alkenyl, $C_{2-6}$ alkynyl, $C_{1-6}$ alkoxy, $C_{3-20}$ carbocyclyl, or $C_{3-20}$ heterocyclyl; and each of $R_5$, $R_5'$, $R_6$, $R_6'$, $R_7$, and $R_7'$, independently, is hydrogen, deuterium, halogen, cyano, hydroxyl, carboxyl, $C_{1-6}$ alkyl, $C_{2-6}$ alkenyl, $C_{2-6}$ alkynyl, $C_{1-6}$ alkoxy, $C_{3-20}$ carbocyclyl, or $C_{3-20}$ heterocyclyl; or $R_5$ and $R_6$, $R_5'$ and $R_6'$, or $R_5$ and $R_5'$, together with the adjacent atom to which they are each attached, form $C_{3-10}$ carbocyclyl or $C_{3-10}$ heterocyclyl, wherein each of $C_{1-6}$ alkyl, $C_{2-6}$ alkenyl, $C_{2-6}$ alkynyl, $C_{1-6}$ alkoxy, $C_{2-6}$ alkenyloxy, $C_{1-6}$ alkylcarbonyl, $C_{1-6}$ alkyloxycarbonyl, $C_{1-6}$ alkylamine, $C_{3-10}$ carbocyclyl, $C_{3-10}$ heterocyclyl, $C_{3-20}$ carbocyclyl, and $C_{3-20}$ heterocyclyl is optionally substituted with 1 to 5 moieties of deuterium, halogen, hydroxyl, cyano, amino, nitro, carboxyl, $C_{1-6}$ alkyl, $C_{1-6}$ alkoxy, $C_{1-6}$ alkylamino, $C_{1-6}$ alkyl($C_{3-10}$ carbocyclyl), $C_{1-6}$ alkyl($C_{3-10}$ heterocyclyl), $C_{1-6}$ alkoxy($C_{3-10}$ carbocyclyl), $C_{1-6}$ alkoxy($C_{3-10}$ heterocyclyl), $C_{3-10}$ carbocyclyl, or $C_{3-10}$ heterocyclyl.

2. The compound, or the pharmaceutically acceptable salt of claim 1, wherein $R_1$ is hydrogen, deuterium, halogen, hydroxyl, $C_{1-6}$ alkyl, or $C_{1-6}$ alkoxy, and each of $R_2$, $R_2'$, $R_3$, and $R_3'$, independently, is hydrogen, deuterium, halogen, hydroxyl, carboxyl, amino, $C_{1-6}$ alkyl, $C_{2-6}$ alkenyl, $C_{1-6}$ alkoxy, $C_{1-6}$ alkylcarbonyl, $C_{1-6}$ alkyloxycarbonyl, or $C_{3-20}$ carbocyclyl.

3. The compound, or the pharmaceutically acceptable salt of claim 1, wherein $R_1$ is hydrogen, deuterium or $C_{1-6}$ alkyl, and each of $R_2$, $R_2'$, $R_3$, and $R_3'$, independently, is hydrogen, deuterium, halogen, carboxyl, $C_{1-6}$ alkyl, $C_{1-6}$ alkoxy, $C_{1-6}$ alkylcarbonyl, or $C_{1-6}$ alkyloxycarbonyl.

4. The compound, or the pharmaceutically acceptable salt of claim 1, wherein each of $R_4$, $R_5$, $R_5'$, $R_6$, and $R_6'$, independently, is hydrogen, deuterium, halogen, hydroxyl, $C_{1-6}$ alkyl, $C_{2-6}$ alkenyl, $C_{1-6}$ alkoxy, $C_{3-20}$ carbocyclyl, or $C_{3-20}$ heterocyclyl, and each of $R_7$ and $R_7'$, independently, is $C_{1-6}$ alkyl, $C_{3-20}$ carbocyclyl, or $C_{3-20}$ heterocyclyl, and each of $C_{1-6}$ alkyl, $C_{3-20}$ carbocyclyl, and $C_{3-20}$ heterocyclyl is optionally substituted with 1 to 3 $C_{3-8}$ carbocyclyl or $C_{3-8}$ heterocyclyl.

5. The compound, or the pharmaceutically acceptable salt of claim 4, wherein each of $R_7$ and $R_7'$, independently, is 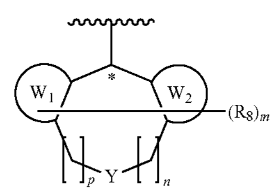 or wherein:
each of $W_1$ and $W_2$, independently, is $C_{3-8}$ carbocyclyl or $C_{3-8}$ heterocyclyl;
Y is O, S, SO, $SO_2$, or $CH_2$;
$R_8$ is hydrogen, deuterium, halogen, hydroxyl, $C_{1-6}$ alkyl, or $C_{1-6}$ alkoxy, wherein $C_{1-6}$ alkyl or $C_{1-6}$ alkoxy is optionally substituted with 1 to 5 deuterium, halogen or hydroxyl groups;
m is an integer of 1 to 5;
n is an integer of 0 to 2;
p is an integer of 0 to 2; and
the star (*) indicates a chiral center.

6. The compound, or the pharmaceutically acceptable salt of claim 5, wherein each of $R_7$ and $R_7'$, independently, is

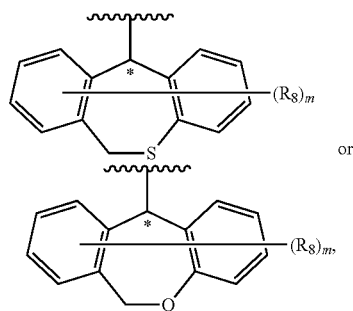

and
wherein m is 1, 2, or 3.

7. The compound, or the pharmaceutically acceptable salt of claim 6, wherein each of $R_7$ and $R_7'$, independently is

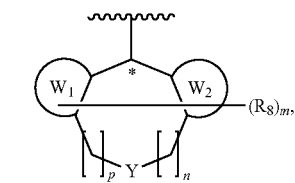

and
wherein each of $R_{14}$, $R_{15}$ and $R_{16}$, independently, is hydrogen or deuterium.

8. The compound, or the pharmaceutically acceptable salt of claim 1, wherein:
$R_1$ is hydrogen, deuterium, halogen, or $C_{1-6}$ alkyl;
each of $R_2$, $R_2'$, $R_3$, and $R_3'$, independently, is hydrogen, deuterium, halogen, hydroxyl, carboxyl, amino, $C_{1-6}$ alkyl, $C_{2-6}$ alkenyl, $C_{1-6}$ alkoxy, $C_{1-6}$ alkylcarbonyl, $C_{1-6}$ alkyloxycarbonyl, or $C_{3-20}$ carbocyclyl;
each of $R_4$, $R_5$, $R_5'$, $R_6$, and $R_6'$, independently, is hydrogen, deuterium, halogen, $C_{1-6}$ alkyl, or $C_{2-6}$ alkenyl; and
each of $R_7$ and $R_7'$, independently, is hydrogen, deuterium, carboxyl, $C_{1-6}$ alkyl, $C_{3-20}$ carbocyclyl, or $C_{3-20}$ heterocyclyl.

9. The compound, or the pharmaceutically acceptable salt of claim 1, wherein:
$R_1$ is hydrogen, deuterium or $C_{1-6}$ alkyl;
each of $R_2$, $R_2'$, $R_3$, and $R_3'$, independently, is hydrogen, deuterium, halogen, carboxyl, $C_{1-6}$ alkyl, $C_{1-6}$ alkoxy, $C_{1-6}$ alkylcarbonyl, or $C_{1-6}$ alkyloxycarbonyl;
each of $R_4$, $R_5$, $R_5'$, $R_6$, and $R_6'$, independently, is hydrogen, deuterium, $C_{1-6}$ alkyl, or $C_{2-6}$ alkenyl; and
each of $R_7$ and $R_7'$, independently, is

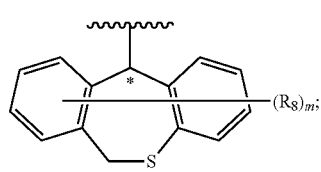

and
wherein:
each of $W_1$ and $W_2$, independently, is $C_{3-8}$ carbocyclyl or $C_{3-8}$ heterocyclyl;
Y is O or S;
$R_8$ is hydrogen, deuterium, halogen, hydroxyl, $C_{1-6}$ alkyl, or $C_{1-6}$ alkoxy, wherein $C_{1-6}$ alkyl or $C_{1-6}$ alkoxy is optionally substituted with 1 to 5 deuterium, halogen or hydroxyl groups;
m is an integer of 1 to 5;
n is an integer of 0 to 2;
p is an integer of 0 to 2; and
the star (*) indicates a chiral center.

10. The compound, or the pharmaceutically acceptable salt of claim 1, wherein $A_1$ is $CR_4$, $A_2$ is $NR_7$ and $A_3$ is $CR_5'R_6'$.

11. The compound, or the pharmaceutically acceptable salt of claim 1, wherein:
$A_1$ is CH;
$A_2$ is $NR_7$;
$A_3$ is $CR_5'R_6'$;
$R_1$ is hydrogen, deuterium or $C_{1-6}$ alkyl;
each of $R_2$, $R_2'$, $R_3$, and $R_3'$, independently, is hydrogen, deuterium, halogen, carboxyl, $C_{1-6}$ alkyl, $C_{1-6}$ alkoxy, $C_{1-6}$ alkylcarbonyl, or $C_{1-6}$ alkyloxycarbonyl;
each of $R_5'$ and $R_6'$, independently, is hydrogen, deuterium, $C_{1-6}$ alkyl, or $C_{2-6}$ alkenyl;
$R_7$ is

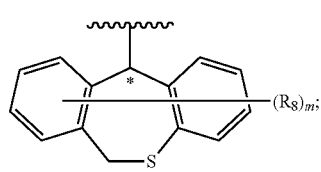

and
$R_8$ is hydrogen, deuterium, halogen, hydroxyl, $C_{1-6}$ alkyl, or $C_{1-6}$ alkoxy, wherein $C_{1-6}$ alkyl or $C_{1-6}$ alkoxy is optionally substituted with 1 to 5 deuterium, halogen or hydroxyl groups.

12. The compound, or the pharmaceutically acceptable salt of claim 1, wherein the compound is one of the following compounds:

Compound 1
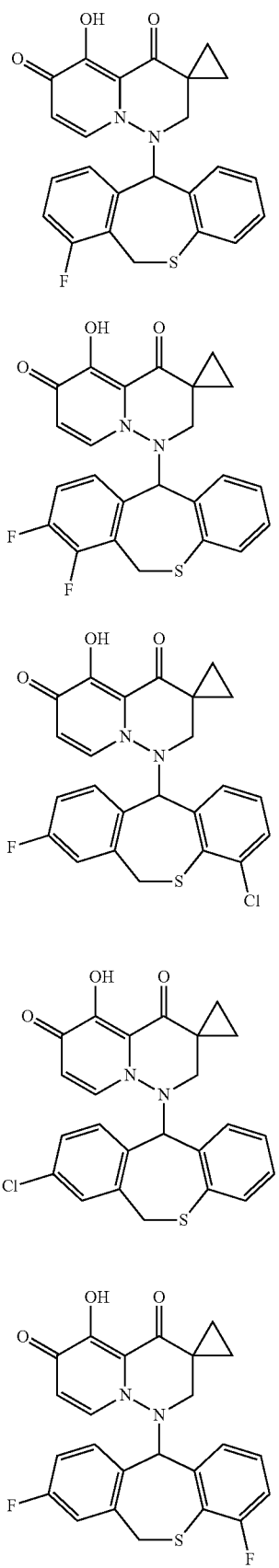
Compound 2
Compound 3
Compound 4
Compound 5
Compound 6
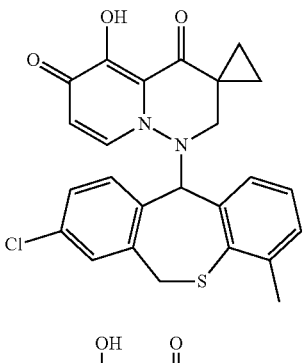
Compound 7
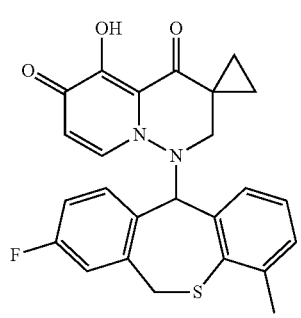
Compound 8
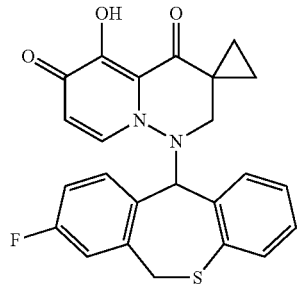
Compound 9
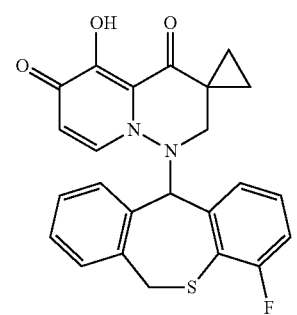
Compound 10
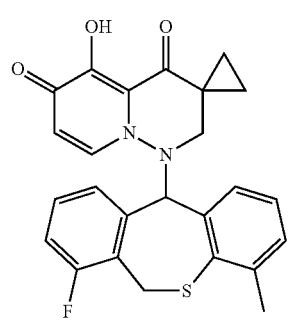

Compound 11
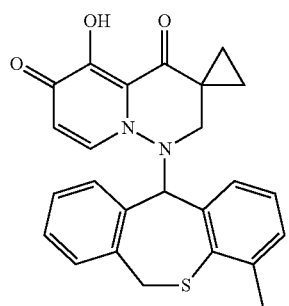
Compound 16
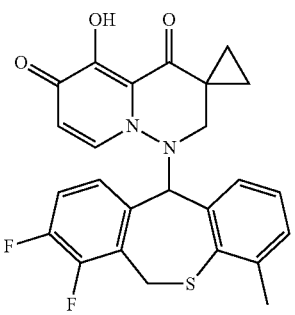
Compound 12
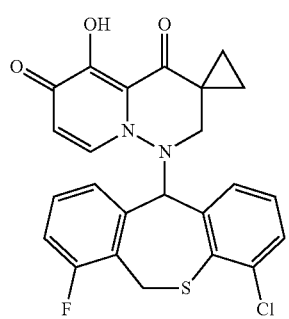
Compound 17
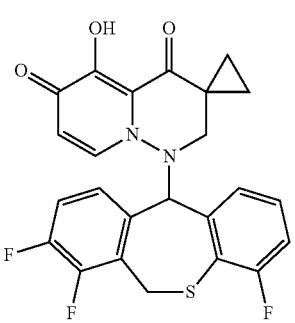
Compound 13
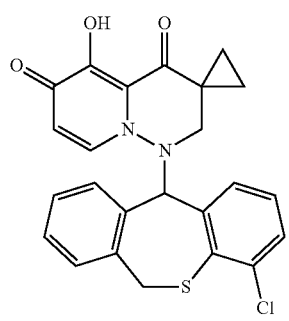
Compound 18
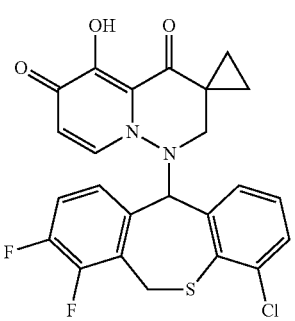
Compound 14
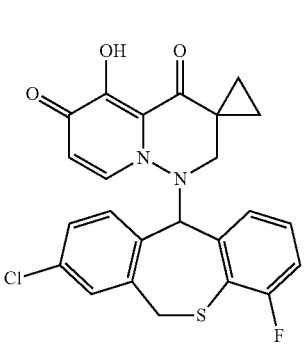
Compound 19
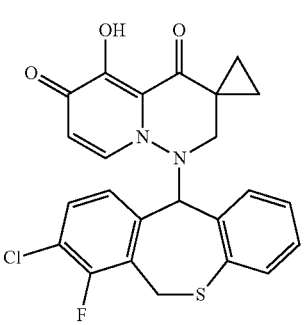
Compound 15
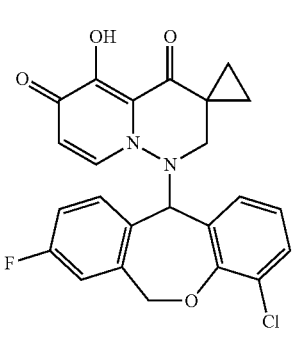
Compound 20
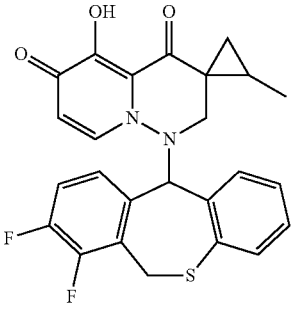

Compound 21
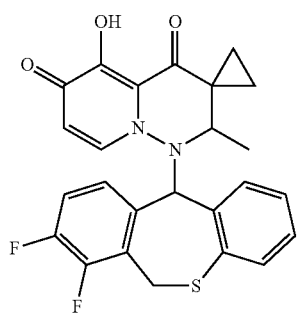
Compound 22
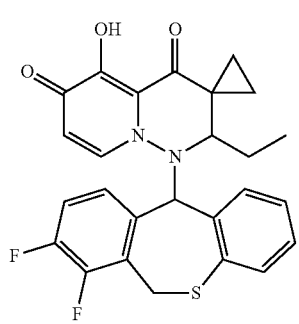
Compound 23
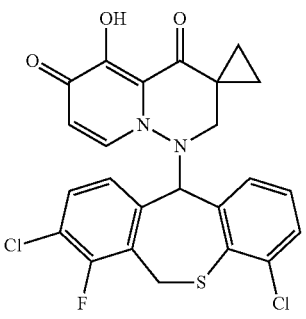
Compound 24
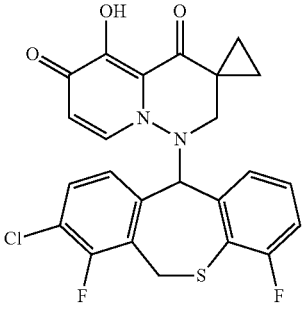
Compound 25
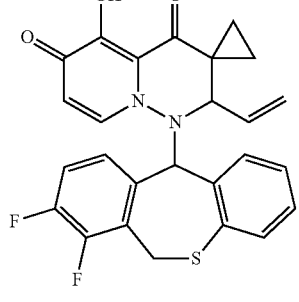
Compound 26
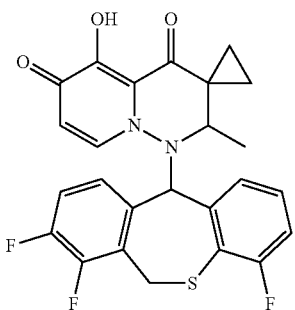
Compound 27
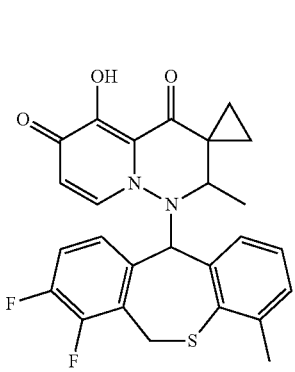
Compound 28
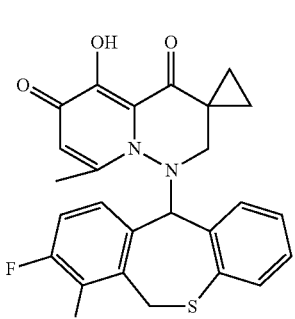
Compound 29
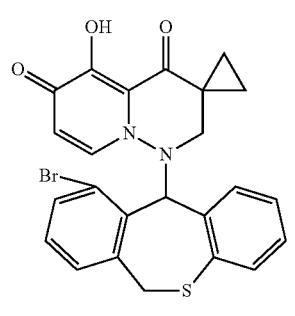
Compound 30
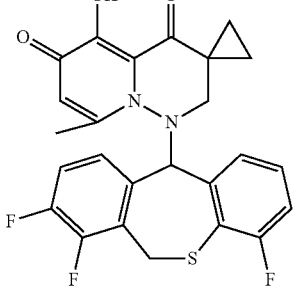

Compound 31
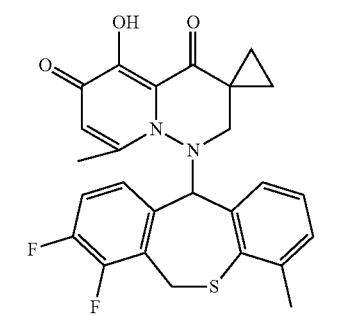
Compound 32
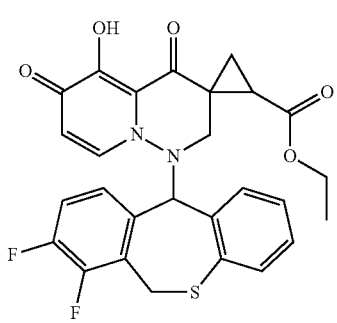
Compound 33
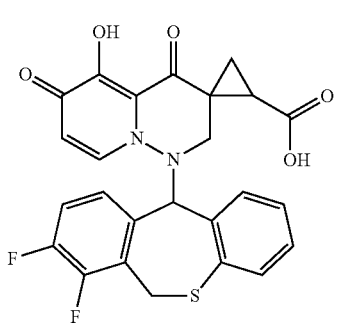
Compound 34
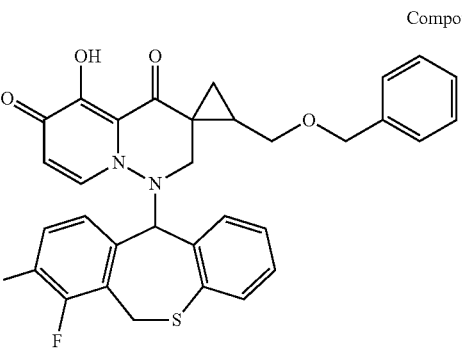
Compound 35
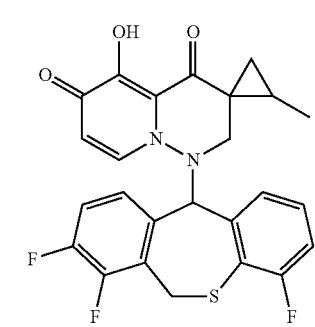
Compound 36
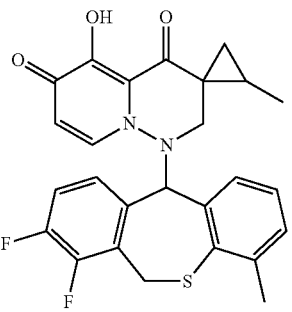
Compound 37
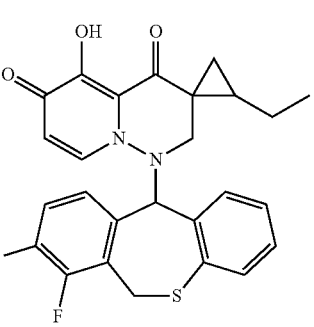
Compound 38
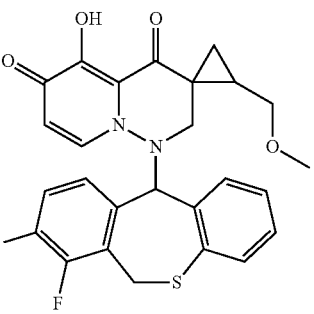
Compound 39
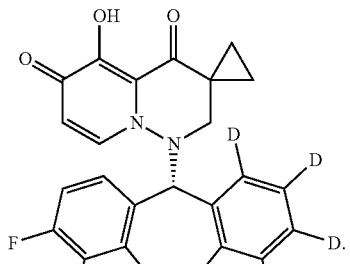
13. The compound, or the pharmaceutically acceptable salt of claim 1, wherein the compound has the following formula:
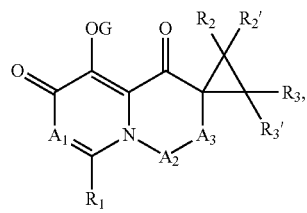

wherein G is —C(R₉R₉')—O—CO—R₁₀, —C(R₉R₉')—O—CO—O—R₁₀, —C(R₉R₉')—NR₁₁—C(=O)—CO—O—R₁₀, —C(R₉R₉')—O—CO—C(R₉R₉')—NR₁₁—CO—O—R₁₀, —C(R₉R₉')—C(R₉R₉')—O—CO—R₁₀, —C(R₉R₉')—R₁₀, —C(=O)—O—R₁₀, —C(=O)—R₁₀, —C(=O)—O-alkylene-O—R₁₀, —C(=O)—NR₁₀R₁₁, or —P(=O)(R₁₂R₁₃), and wherein each of R₉, R₉', and R₁₁, independently, is hydrogen or C₁₋₈ alkyl; R₁₀ is C₁₋₈ alkyl, C₃₋₁₀ carbocyclyl, or C₃₋₁₀ heterocyclyl; R₁₂ is C₁₋₈ alkoxy; and R₁₃ is C₁₋₈ alkoxy or C₁₋₈ alkylamine.

14. The compound, or the pharmaceutically acceptable salt of claim 13, wherein G is

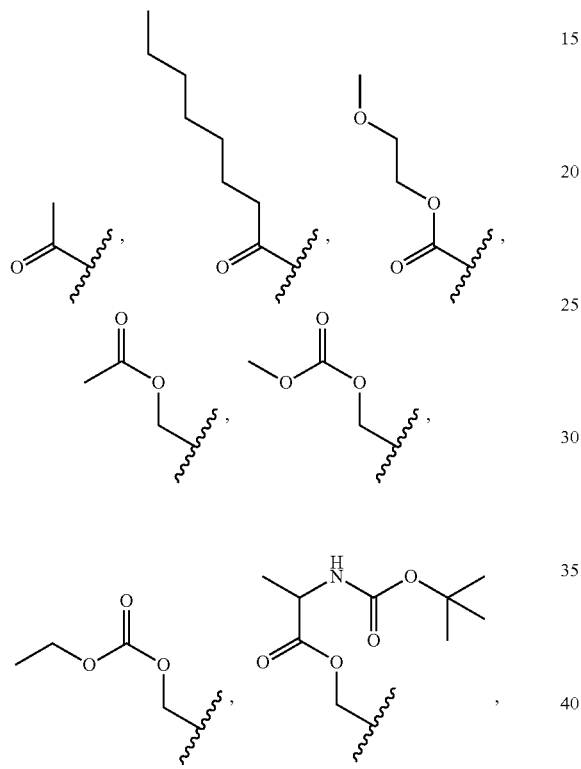

15. The compound, or the pharmaceutically acceptable salt of claim 13, wherein the compound is one of the following compounds:

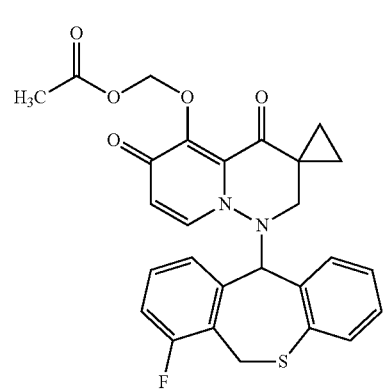

Compound 40

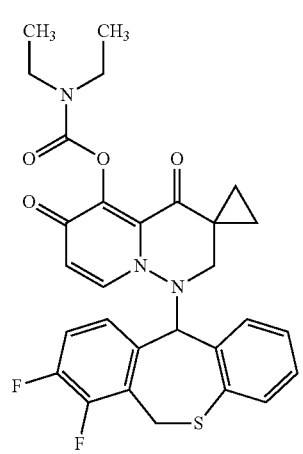

Compound 41

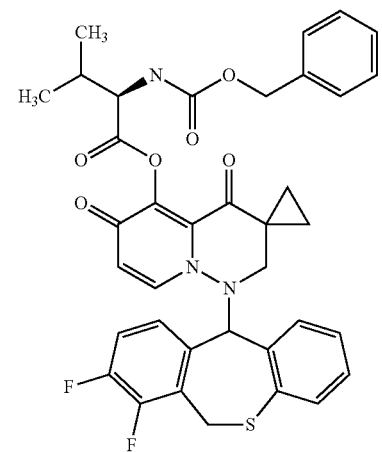

Compound 42

Compound 43
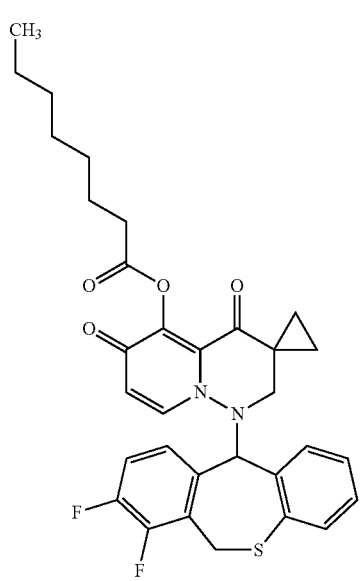
Compound 44
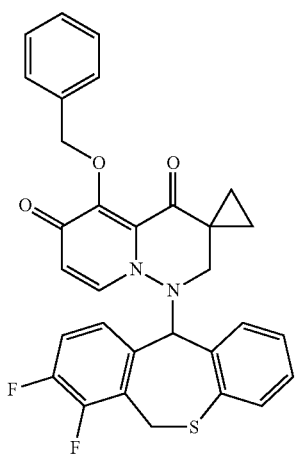
Compound 45
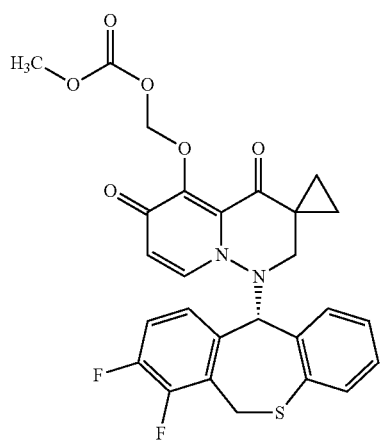
Compound 46
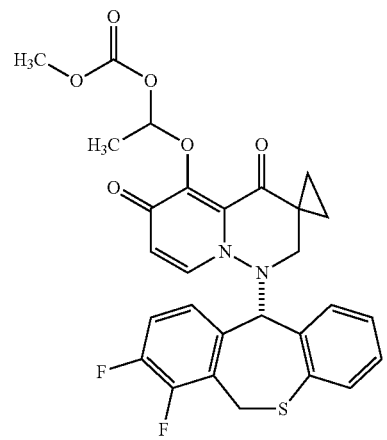
Compound 47
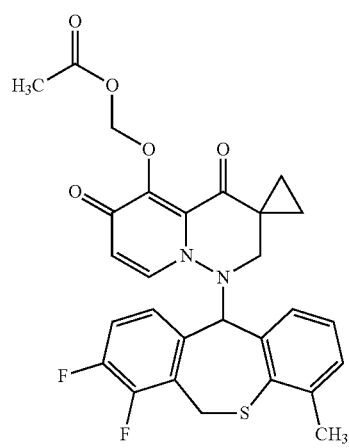
Compound 48
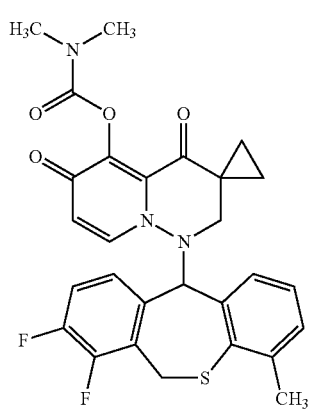

Compound 49
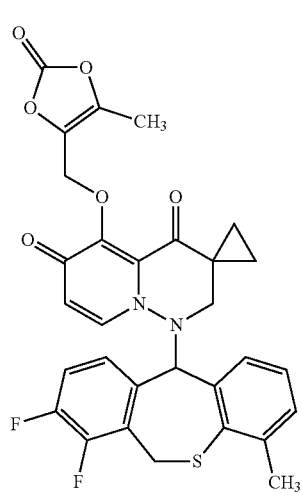
Compound 52
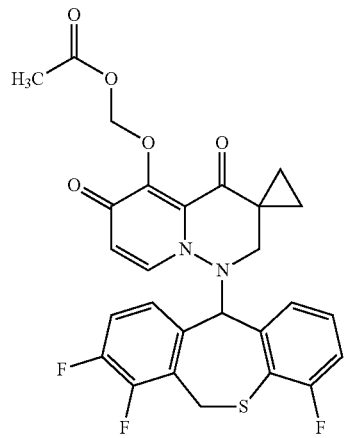
Compound 50
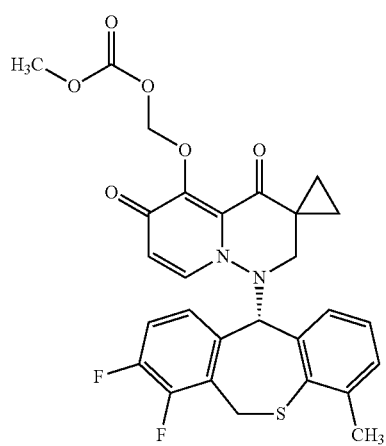
Compound 53
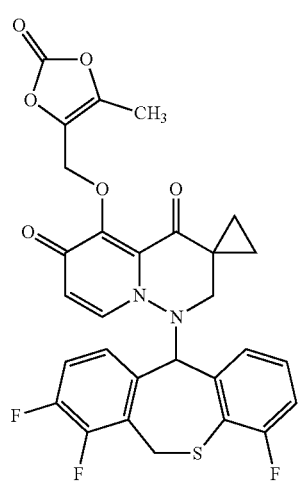
Compound 51
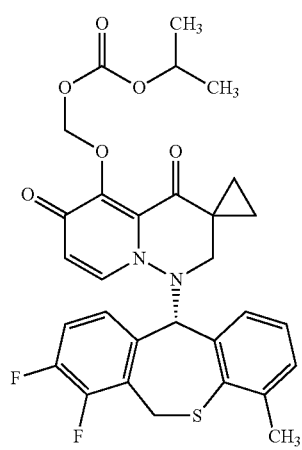
Compound 54
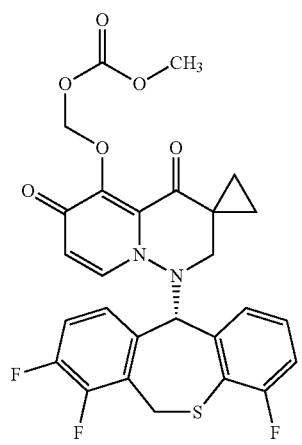

Compound 55

Compound 56

Compound 57

Compound 58

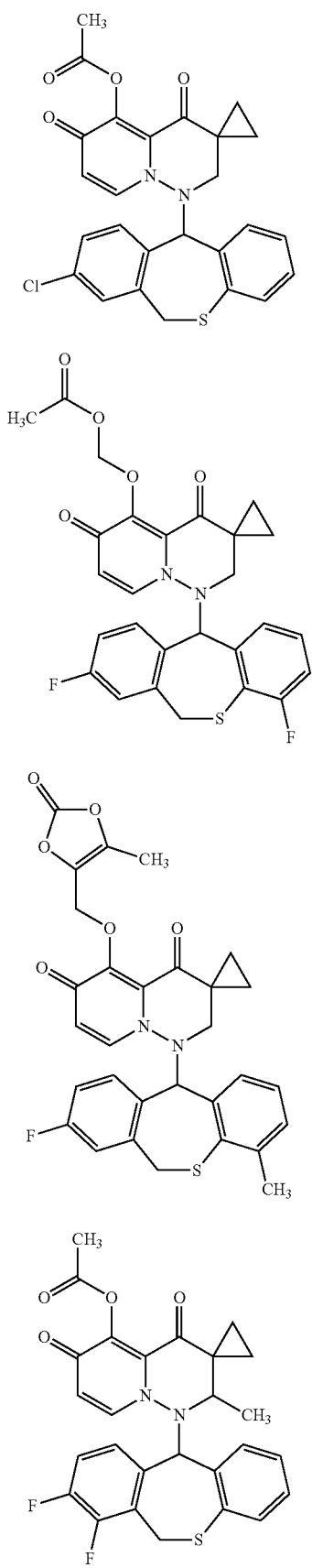

Compound 59

Compound 60

Compound 61

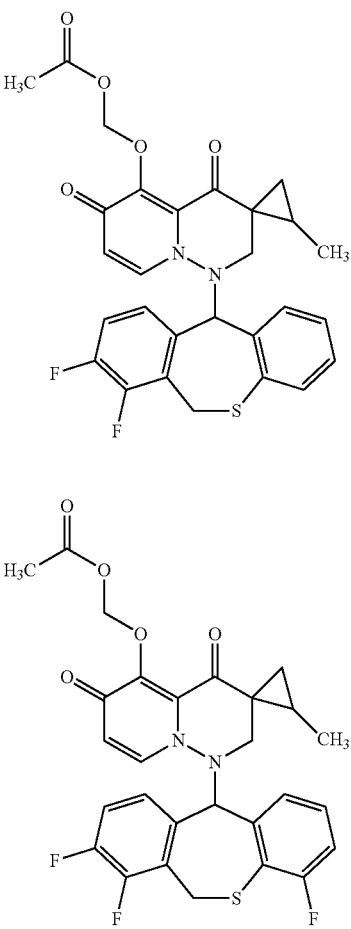

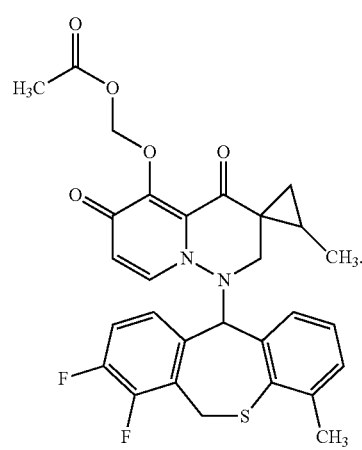

16. A pharmaceutical composition, comprising the compound, or the pharmaceutically acceptable salt of claim 1, and a pharmaceutically acceptable carrier thereof.

17. A method of treating influenza, comprising administering to a subject in need thereof an effective amount of the compound, or the pharmaceutically acceptable salt of claim 1.

18. A method of preparing a compound of Formula (I) below, or a pharmaceutically acceptable salt thereof,

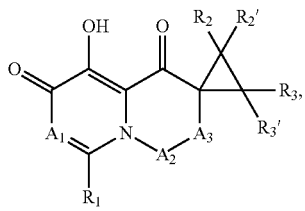

the method comprising:
providing an aldehyde

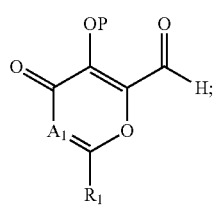

reacting the aldehyde with a carbonyl compound

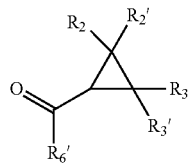

to afford a first intermediate

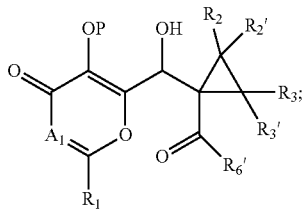

reacting the first intermediate with a hydrazine to afford a second intermediate

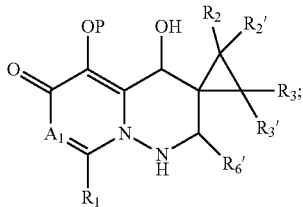

and
converting the second intermediate to the compound of Formula (I), or the pharmaceutically acceptable salt thereof, wherein:
P is a protecting group;
$A_1$ is $CR_4$;
$A_2$ is $NR_7$;
$A_3$ is $CR_5'R_6'$;
$R_1$ is hydrogen, deuterium, halogen, cyano, hydroxyl, carboxyl, amino, $C_{1-6}$ alkyl, $C_{2-6}$ alkenyl, $C_{2-6}$ alkynyl, $C_{1-6}$ alkoxy, $C_{1-6}$ alkylamine, $C_{3-20}$ carbocyclyl, or $C_{3-20}$ heterocyclyl;
each of $R_2$, $R_2'$, $R_3$, and $R_3'$, independently, is hydrogen, deuterium, halogen, cyano, hydroxyl, carboxyl, amino, formyl, nitro, $C_{1-6}$ alkyl, $C_{2-6}$ alkenyl, $C_{2-6}$ alkynyl, $C_{1-6}$ alkoxy, $C_{2-6}$ alkenyloxy, $C_{1-6}$ alkylcarbonyl, $C_{1-6}$ alkyloxycarbonyl, $C_{1-6}$ alkylamine, $C_{3-20}$ carbocyclyl, or $C_{3-20}$ heterocyclyl;
$R_4$ is hydrogen, deuterium, halogen, cyano, hydroxyl, carboxyl, amino, $C_{1-6}$ alkyl, $C_{2-6}$ alkenyl, $C_{2-6}$ alkynyl, $C_{1-6}$ alkoxy, $C_{3-20}$ carbocyclyl, or $C_{3-20}$ heterocyclyl;
$R_5'$ is H; and
each of $R_6'$ and $R_7$, independently, is hydrogen, deuterium, halogen, cyano, hydroxyl, carboxyl, $C_{1-6}$ alkyl, $C_{2-6}$ alkenyl, $C_{2-6}$ alkynyl, $C_{1-6}$ alkoxy, $C_{3-20}$ carbocyclyl, or $C_{3-20}$ heterocyclyl, and
wherein each of $C_{1-6}$ alkyl, $C_{2-6}$ alkenyl, $C_{2-6}$ alkynyl, $C_{1-6}$ alkoxy, $C_{2-6}$ alkenyloxy, $C_{1-6}$ alkylcarbonyl, $C_{1-6}$ alkyloxycarbonyl, $C_{1-6}$ alkylamine, $C_{3-20}$ carbocyclyl, and $C_{3-20}$ heterocyclyl is optionally substituted with 1 to 5 moieties of deuterium, halogen, hydroxyl, cyano, amino, nitro, carboxyl, $C_{1-6}$ alkyl, $C_{1-6}$ alkoxy, $C_{1-6}$ alkylamino, $C_{1-6}$ alkyl($C_{3-10}$ carbocyclyl), $C_{1-6}$ alkyl ($C_{3-10}$ heterocyclyl), $C_{1-6}$ alkoxy($C_{3-10}$ carbocyclyl), $C_{1-6}$ alkoxy($C_{3-10}$ heterocyclyl), $C_{3-10}$ carbocyclyl, or $C_{3-10}$ heterocyclyl.

* * * * *